United States Patent [19]

Kampe et al.

[11] Patent Number: 4,818,758
[45] Date of Patent: Apr. 4, 1989

[54] 2-AZOLYLMETHYL-2-PHENYL-4-[BENZAZOL-2-YLOXY-OR-THIO-METHYL]-1,3 DIOXOLANES AND SALTS THEREOF, PHARMACEUTICAL COMPOSITIONS CONTAINING THEM AND THEIR USE

[75] Inventors: Klaus-Dieter Kampe, Bad Soden am Taunus; Wolfgang Raether, Dreieich; Walter Dittmar, Hofheim am Taunus, all of Fed. Rep. of Germany

[73] Assignee: Hoechst Aktiengesellschaft, Frankfurt am Main, Fed. Rep. of Germany

[21] Appl. No.: 28,173

[22] Filed: Mar. 19, 1987

[30] Foreign Application Priority Data

Mar. 21, 1986 [DE] Fed. Rep. of Germany ....... 3609597

[51] Int. Cl.[4] ................. A61K 31/335; A61K 31/415; C07D 405/14
[52] U.S. Cl. .................................... 514/252; 514/253; 514/254; 514/367; 514/375; 514/383; 514/394; 544/366; 544/367; 544/368; 544/369; 548/165; 548/221; 548/262
[58] Field of Search ............... 544/366, 367, 368, 369, 544/370; 514/252, 253, 254, 394, 375, 367, 383; 548/262, 165, 221

[56] References Cited

U.S. PATENT DOCUMENTS

| | | | |
|---|---|---|---|
| 4,144,346 | 3/1979 | Heeres et al. | 544/370 |
| 4,267,179 | 5/1981 | Heeres et al. | 544/370 |
| 4,287,195 | 9/1981 | Heeres et al. | 544/366 |
| 4,335,125 | 6/1982 | Heeres et al. | 544/370 |
| 4,368,200 | 1/1983 | Heeres et al. | 544/370 |
| 4,391,805 | 7/1983 | Blume et al. | 544/370 |
| 4,402,957 | 9/1983 | Heeres et al. | 544/368 |
| 4,490,530 | 12/1984 | Heeres et al. | 544/370 |
| 4,503,055 | 3/1985 | Heeres et al. | 544/370 |
| 4,634,700 | 1/1987 | Schickaneder et al. | 544/370 |

FOREIGN PATENT DOCUMENTS

| | | | |
|---|---|---|---|
| 7696 | 2/1980 | European Pat. Off. | |
| 118138 | 9/1984 | European Pat. Off. | 544/370 |
| 3410070 | 10/1985 | Fed. Rep. of Germany | 544/370 |

OTHER PUBLICATIONS

Heeres et al. CA93-168303v.
Bergus, Medicinal Chem. 2nd Edition, pp. 42–43.

Primary Examiner—Donald G. Daus
Assistant Examiner—Cecilia Shen
Attorney, Agent, or Firm—Finnegan, Henderson, Farabow, Garrett, & Dunner

[57] ABSTRACT

Compounds of the formula I

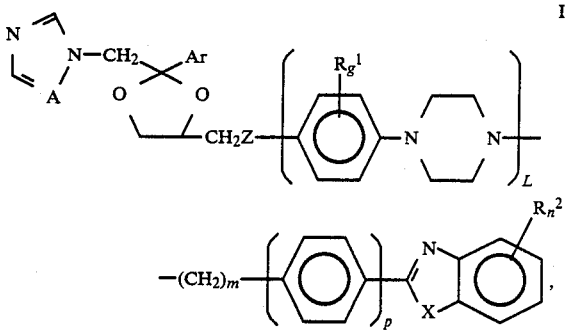

and the acid-addition salts thereof, where A=CH or N; Ar=naphthyl, thienyl or phenyl; Z=oxygen or sulfur; $R^1$=alkyl, F or Cl; g=0-2; L=0 or 1; m=0-4; p=0 or 1; X=O, S or N—$R^3$; $R^2$=alkyl, alkoxy, halogen, $SCH_3$, $COC_6H_5$, $CF_3$, $COOCH_3$, $COOC_2H_5$, or $NO_2$; n=0-2; $R^2$, under certain circumstances, is alternatively —CH=CH—CH=CH— or phenoxy are described. Processes for the preparation thereof are also described.

Compounds IIIa

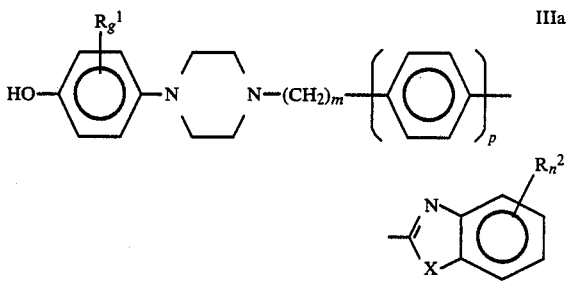

are valuable intermediates for the preparation of I.
The compounds I serve as antimycotics.

7 Claims, No Drawings

2-AZOLYLMETHYL-2-PHENYL-4-[BENZAZOL-2-YLOXY-OR-THIO-METHYL]-1,3 DIOXOLANES AND SALTS THEREOF, PHARMACEUTICAL COMPOSITIONS CONTAINING THEM AND THEIR USE

The invention relates to 2-azolylmethyl-2-aryl-4-[(4-piperazinophenoxy)methyl]-1,3-dioxolanes, including the salts thereof, which are substituted by benzazolyl radicals, processes for the preparation thereof, medicaments containing these compounds, and the use thereof, particularly as antimycotics.

2-Azolylmethyl-2-aryl-4-[(4-piperazinophenoxy)methyl]-1,3-dioxolanes which have an antimycotic or fungicidal action are already known and are described, inter alia, in German Offenlegungsschrift No. 2,804,096 and European Offenlegungsschrift No. 7,696. The best known representatives from the large number of compounds described are 2-S,(R)-(2,4-dichlorophenyl)-2-(imidazol-1P-ylmetyl)-4-R,(S)-[4-(4-acetylpiperazin-1-yl)phenoxymethyl]-1,3-dioxolane (ketoconazole) and 2-S,(R)-(2,4-dichlorophenyl)-2-(1,2,4-triazol-1-ylmethyl)-4-R,(S)-[4-(4-isopropylpiperazin-1-yl)phenoxymethyl]1,3-dioxolane (terconazole), which are commercially available as antimycotics (cf. German Offenlegungsschrift No. 2,804,096, Example 20 and Example 53), ketoconazole being used mainly as a systemically active antimycotic, and terconazole as a topically active anitmycotic. However, the antimycotic action and, in particular, the toleration of the known compounds are not always completely satisfactory.

It has now been found that 2-azolylmethyl-2-aryl-4-[(4-piperazinophenoxy)methyl]-1,3-dioxolanes of the formula I in which A denotes CH or N, Ar denotes naphthyl, thienyl, halothienyl or a phenyl group which is unsubstituted or carries one to 3 substituents, where the substituents may be identical or different an denote F, Cl, Br, I, $CF_3$, $OCH_3$, $OC_2H_5$, $CH_3$, $C_2H_5$, $C_6H_5$ or phenoxy, Z denotes O or, if L, m and n simultaneously denote zero, denotes O or S, $R^1$ denotes $C_1$-$C_3$-alkyl, F or Cl, g denotes 0, 1 or 2, L denotes 0 or 1, m denotes 0, 1, 2, 3 or 4, p denotes 0 or, if m does not equal 0 or if L and m are simultaneously 0, denotes 0 or 1, X denotes O or, if m does not equal 0, or if L, m and p are simultaneously 0, or if, simultaneously m and p are 0 and n does not equal 0, denotes O, S or N-$R^3$, where $R^3$ denotes H, $C_1$-$C_4$-alkyl, phenyl or benzyl, $R^2$, independently of one another, denote $C_1$-$C_4$-alkyl, $C_1$-$C_4$-alkoxy, F, Cl, Br, I, $SCH_3$, CO-$C_6H_5$, $CF_3$, $COOCH_3$, $COOC_2H_5$ or $NO_2$, n denotes 0, 1 or 2, or, if n is 2, $R^2$, additionally, denotes a —CH=CH—CH=CH group, which, together with the phenyl ring, forms a naphthyl radical, or, if, simultaneously, p is 0 and n is 1, and $R^2$, additionally, represents a phenoxy group which is unsubstituted or carries up to 2 identical or different substitutents on the phenyl radical, the substituents denoting F, Cl, Br, $OCH_3$, $CH_3$ or $C_2H_5$, and the physiologically acceptable acid-addition salts thereof, have valuable antimycotic or fungicidal properties. They are therefore suitable for combaing mycosis in humans and animals and for combating fungal infestations in plants and on materials. a thienyl radical which is linked in the 2 or 3 position and which may be substituted in any position by F, Cl, Br or I, preferably Br or Cl, the terms "$C_1$-$C_3$-alkyl and $C_1$-$C_4$-alkyl" are taken to mean an unbranched or branched hydrocarbon radical having 1-3 or 1-4 carbon atoms respectively, and the term "$C_1$-$C_4$-alkoxy" is taken to mean an alkoxy group, the hydrocarbon radical of which has the meaning specified under the term "$C_1$-$C_4$-alkyl".

Preferred compounds of the formula I are those in which at least one of the substituents or indices have the following meaning:

A denotes CH or N,

Ar denotes a phenyl group which is substituted by 1 or 2 F or Cl atoms,

Z denotes O or, if L, m and p simultaneously denote zero, denotes O or S, $R^1$ denotes $CH_3$ or $C_2H_5$, g denotes 0 or 2, L denotes 0 or 1, m denotes 0, 1, 2 or 3, p denotes 0 or, if m is 1, denotes 0 or 1, X denotes O, or, if m is 1, 2 or 3, or if L and m are simultaneously 0, or if, simultaneously, m is 0 and n is 1 or 2, denotes O or S, $R^2$ independently of one another, denote $C_1$-$C_4$-n-alkyl, $C_1$-$C_4$-alkoxy, F, Cl, Br or, if p is 0 and n is 1, $OC_6H_5$, and n denotes 0, 1 or 2.

In this connection, the term "$C_1$-$C_4$-n-alkyl" is taken to mean a straight-chain alkyl radical having 1-4 carbon atoms.

Particularly preferred compounds of the formula I are those in which at least one of the substituents or indices has the following meaning:

A denotes CH or N,

Ar denotes 2,4-dichlorophenyl,

Z denotes O, $R^1$ denotes $CH_3$, g denotes 0 or 2,

L denotes 0 or 1, m denotes 0, 1, 2 or 3, p denotes 0 or, if m is 1, denotes 0 or 1, X denotes O or, if m is 1, 2 or 3 or if L and m are simultaneously 0, denotes O or S, $R^2$, independently of one another, denote $CH_3$, $C_2H_5$, $C_1$-$C_4$-alkoxy, F, Cl or Br, and n denotes 0, 1 or 2.

Particularly preferred compounds of the formula I are furthermore those in which L, m and p simultaneously denote zero, or L denotes zero and, simultaneously, m and p denotes 1 and in each case X denotes O or S and n denotes zero or 1, and R², independently of one another, denote CH₃, C₂H₅, C₁-C₄-alkoxy, F, Cl or Br.

The invention furthermore relates to the possible stereoisomers of the formula I, both as diastereomer racemates and as pure enantiomers, and to the pharmaceutically acceptable salts thereof. In particular, this concerns the stereoisomers which are possible as a result of the 2,4-disubstitution of the 1,3-dioxolane ring; the 2-azolylmethyl group may be located in the cis or trans position to the substituent in the 4 position, the substituted phenoxymehtyl group. The cis isomers are included in the preferred compounds according to the invention.

Suitable salts of the compounds of the formula I according to the invention are those with physiologically acceptable inorganic and organic acids, such as, for example, hydrochloric acid, hydrobromic acid, hydroiodic acid, sulfuric acid, phosphoric acid, nitric acid, benzinesulfonic acid, toluenesulfonic acid, sulfamic acid, methylsulfuric acid, acetic acid, propionic acid, oleic acid, palmitic acid, stearic acid, malonic acid, maleic acid, succinic acid, glutaric acid, malic acid, tartaric acid, citric acid, fumaric acid, lactic acid, glycolic acid, pyruvic acid, benzoic acid, toluic acid, glutamic acid, furancarboxylic acid, salicyclic acid or mandelic acid. Preferred salts are those with physiologically acceptable inorganic acids, strong to medium-strength acidic derivatives of such acids, or with fumaric acid.

The compounds according to the invention differ from the known, abovementioned azolylmethyl-2-aryl-4-[(4-piperazinophenoxy)methyl]-1,3-dioxolanes which are active against fungi and bacteria essentially through the structure of the substituent in the 4 position of the dioxolane ring. The compounds according to the invention differ from the compounds mentioned in EP-A No. 7,696, to some if which they are similar, either through a different structure of the substituents in the 4 position of the 1,3-dioxolane or through the type and position of the substituents on the benzazole units.

Surprisingly, the 2-azolyl-2-aryl-4-[(4-piperazinophenoxy)methyl]-1,3-dioxolanes exhibit a broader and better antimycotic action than the known 2-azolylmethyl-2-aryl-1,3-dioxolane derivatives and the known 2-S,(R)-(2,4-dichlorophenyl)-2-(imidazol-1-ylmethyl)-4-R,(S)-[4-(4-acetylpiperazin-1-yl)phenoxymethyl]-1,3-dioxolane (ketoconazole).

The invention furthermore relates to a process for the preparation of compounds of the formula I and the salts thereof, wherein (A) a compound of the formula II,

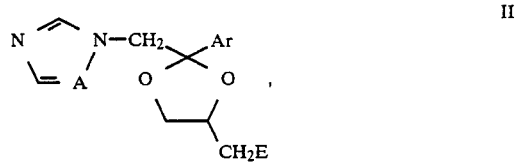

in which

A and Ar have the meanings specified in the case of the formula I, and

E denotes Cl, Br, I or acyloxy, such as acetoxy, trifluoroacetyloxy, benzoyloxy, nitrobenzoyloxy, C₁-C₃-alkylsulfonyloxy, such as methanesulfonyloxy, or arylsulfonyloxy, such as benzene-, nitrobenzene-, bromobenzene- or toluenesulfonyloxy, is reacted with a compound of the formula III

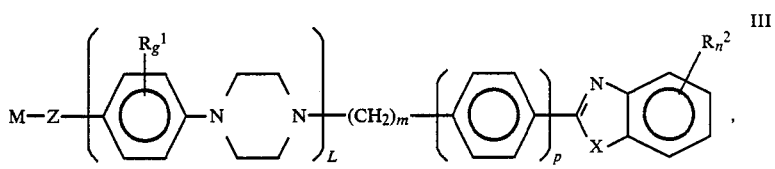

in which

Z denotes O or, if L, m and p simultaneously denote zero, denotes S,

M denotes H, an alkali metal or alkaline-earth metal, particularly Li, Na or K, or NH₄, and R¹, g, L, m, p, X, R² and n have the meanings specified in the case of the formula I, or wherein (B) a compound of the formula IV

in which

Ar has the meanings specified in the case of the formula I, and E and E' have the meanings specified for E in the case of the formula II, is initially reacted with a compound of the formula III,

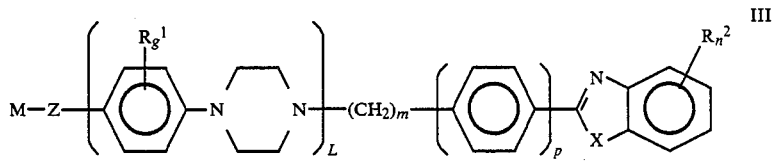

a compound of the formula V

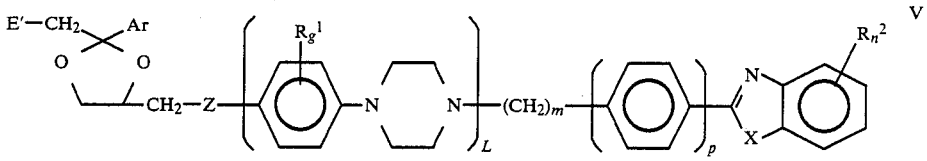

in which Z denotes O or, if L, m and p simultaneously denote zero, denotes S, and Ar, $R^1$, g. L, m, p, X, $R^2$ and n have the meanings specified in the case of the formula I, and E' has the meanings specified for E in the case of the formula II, being prepared here, and a compound of the formula V is subsequently reacted with a compound of the formula VI,

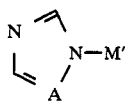

in which
A denotes CH or N and
M' denotes H, an alkali metal, an alkaline-earth metal or $Si(CH_3)_3$,
or wherein
(C) a compound of the formula VII

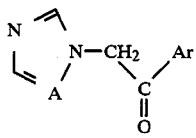

in which A and Ar have the meanings specified in the case of the formula I, is reacted with a 1,2-diol of the formula VIII

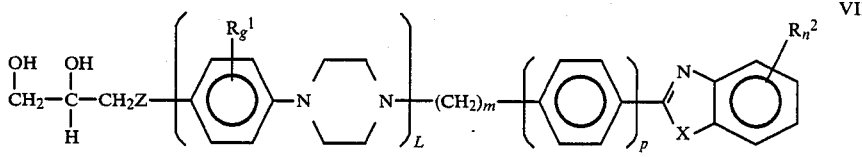

in which Z, $R^1$, g, L, m, p, X, $R^2$ and n have the meanings specified in the case of the formula I, or wherein
(D) a compound of the formula IX,

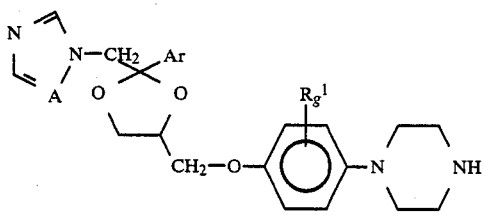

in which A, Ar, $R^1$ and g have the meanings specified in the case of the formula I, or a salt of this compound, is reacted either with a compound of the formula X,

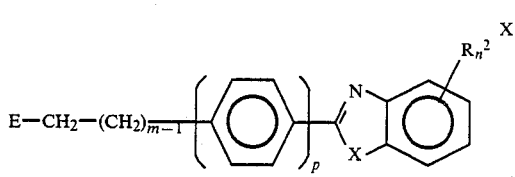

in which E denotes Cl, Br, I, acyloxy, such as acetyloxy, trifluoroacetyloxy, benzoyloxy, nitrobenzoyloxy, $C_1$-$C_3$-alkylsulfonyloxy, such as methanesulfonyloxy, or arylsulfonyloxy, such as benzene-, nitrobenzene-, bromobenzene- or toluenesulfonyloxy,
m denotes 1, 2, 3 or 4, and
p, X, $R^2$ and n have the meanings specified in the case of the formula I,
or with a compound of the formula XI,

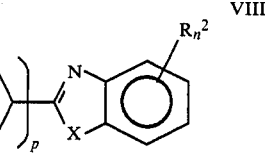

in which
Hal denotes Cl, Br or I, preferably Cl,
X denotes O, or, if n does not eqal O, denotes 0, S or $NR^3$, where
$R^3$ denotes H, $C_1$-$C_4$-alkyl, phenyl or benzyl, and

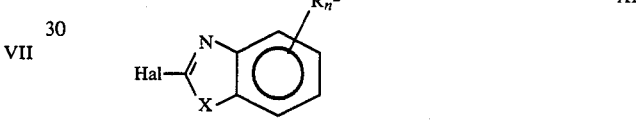

$R^2$ and n have the meanings specified in the case of the formula I, or wherein
(E) a compound of the formula IIa,

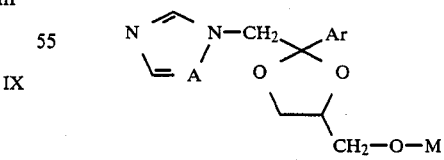

in which A and Ar have the meanings specified in the case of the formula I, and
M denotes H, an alkali metal or alkaline-earth metal, particularly Li, Na or K,
is reacted with a compound of the formula X, in which
E, m, p, X, $R^2$ and n have the meanings specified in the case of the formula X, with formation of a compound of the formula I in which Z denotes O, and A, Ar, $R^1$, g, m, p, X, $R^2$ and n have the specified meanings, and L denotes 0. or wherein (F) a compound of the formula IIa,

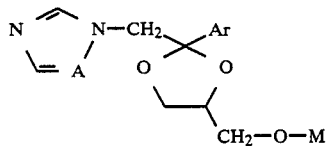

in which A and Ar have the meanings specified in the case of the formula I, and

M denotes H, an alkali metal or alkaline-earth metal, particularly Li, Na or K, is reacted with a compound of the formula XI,

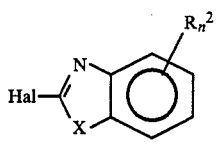

in which p1 Hal denotes Cl, Br or I, preferably Cl, and X, $R^2$ and n have the meanings specified in the case of the formula I, with formation of a compound of the formula I in which Z denotes O, and A, Ar, $R^1$, g, X, $R^2$ and n have the specified meanings, and L, m and p simultaneously denote 0, and the compounds of the formula I obtained by route (A)–(F) are converted if appropriate into their physiologically acceptable salts with inorganic or organic acids.

In this connection, the term "acyloxy" is taken to mean a straight-chain or branched $C_1$–$C_4$-alkanoyloxy radical, a trifluoroacetyl or trichloroacetyl radical or a benzoyloxy radical which is unsubstituted in the phenyl nucleus by up to 2 identical or different substituents, where the substituents may denote $CH_3$, $OCH_3$, F, Cl, Br or $CH_3$, the term "arylsulfonyloxy" is taken to mean a phenylsulfonyloxy or naphthylsulfonyloxyradical which is unsubstituted or substituted by Cl, Br, $CH_3$, $C_2H_5$, $OCH_3$, $OC_2H_5$ or $NO_2$, and the term "$C_1$–$C_3$-alkylsulfonyloxy" is taken to mean an n-alkanesulfonic acid radical having 1–3 carbon atoms. The term "alkali metal" is to denote Li, Na or K.

The process version (A), where, in the compounds of the formula II, E preferably denotes Cl, Br, acetoxy, trifluoroacetoxy, methanesulfonyloxy or (substituted) phenylsulfonyloxy, and, in the compounds of the formula III, M, Z, $R^1$, g, p, X, $R^2$ and n have the specified meanings, and L preferably denote 1, and m preferably denotes 0, 1, 2 or 3, or preferably, L and m simultaneously denote 0, or L, m and p simultaneously denote 0, is carried out at a temperature between 20° C. and 150° C., advantageously between 40° C. and 110° C., in the presence of a base and expediently in an inert organic solvent, such as, for example, N,N-dimethylformamide, N,N-dimethylacetamide, dimethyl sulfoxide, N-methyl-2-pyrrolidone, 1,2-dimethoxyethane, dioxane, tetrahydrofuran, 4-methyl-2-pentanone, methanol, ethanol, isopropyl alcohol, propanol, butanol, pentanol, tert.-butyl alcohol, methyl glycol, methylene chloride, acetonitrile or an aromatic hydrocarbon, such as benzene, chlorobenzene, toluene or xylene. Mixtures of the solvents mentioned as examples may also be used.

Suitable bases are, for example, alkali metal or alkaline-earth metal carbonates, hydrogen carbonated, hydroxides, amides, alcoholates or hydrides, such as, for example, sodium carbonate, sodium hydrogen carbonate, potassium carbonate, sodium hydroxide, sodium amide, sodium methylate, potassium t-butylate or sodium hydride, or organic bases, for example tertiary amines, such as triethylamine, tributylamine, ethylmorpholine or pyridien, dimethylaminopyridine, quinoline of 1,5-diazabicyclo[5,4,0]undec-5-ene (DBU).

The reaction can likewise be carried out under the conditions of a phase-transfer reaction by allowing the reactants to act on one another in a suitable solvent, such as, for example, ether, dioxane, tetrahydrofuran, methylene chloride, N,N-dimethylformamide, N,N-dimethylacetamide, N-methyl-2-pyrrolidone, butanol, tert-butanol, an aliphatic, cycloaliphatic or aromatic hydrocarbon, such as hexane, cyclohexane, benzene, toluene or xylene, methyl glycol, anisole or chlorobenzene, with vigorous stirring in the presence of a phase-transfer catalyst and either a powdered alkali metal hydroxide, such as, for example, sodium hydroxide or potassium hydroxide, or a concentrated aqueous solution thereof, preferably in a temperature range from 20° C. to 120° C.

Suitable phase-transfer catalysts are, for example, trialkylbenzylammonium or tetraalkylammonium halides, hydroxides or hydrogen sulfates, preferably having 1 to 12 carbon atoms in the alkyl radical, or crown ethers, such as, for example, 12-crown-4, 15-crown-5, 18-crown-6 or dibenzo-18-crown-6.

PREPARATION OF THE STARTING MATERIALS

Some of the starting compounds of the formula II in which Ar and A have the meanings specified in the case of the formula I are known; those which are not known may be prepared analogously to those which are known.

Some of the starting compounds of the formula III in which L and m denote 0 and p denotes 1 are known or can be prepared analogously to the known compounds. Those in which L denotes 0, m denotes 1, 2 or 3, preferably 1, and p denotes 0 or 1 can be prepared from the corresponding known chloro or bromo compounds of the formula Xa

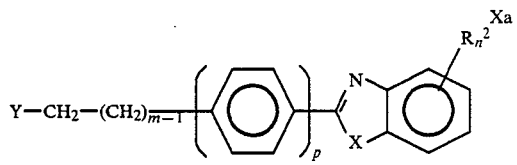

(Y=Cl or Br) by alkaline hydrolysis. Some of the compounds of the formula III in which L, m and p simultaneously denote 0 and Z denotes S are known or can be prepared by known methods, in the case of certain representatives, for example, starting from appropriate 2-chloroanilines and sodium ethylxanthate.

The process version (B), where a compound of the formula IV in which E preferably denotes Br, I or trifluoroacetyloxy, methanesulfonyloxy, benzene-, nitrobenzene-, bromobenzene- or toluenesulfonyloxy, and E' preferably denotes Cl or Br is reacted with a compound of the formula III in which M, Z, $R^1$, g, L, m, p, X, $R^2$ and n have the specified meanings, and L preferably denotes 1 or L and m simultaneously or L, m and p simultaneously denote zero, with formation of a compound of the formula V, is carried out under the same reaction conditions as in the case of version A for the preparation of compounds of the formula I.

The preparation of the compounds of the formula I by reaction of compounds of the formula V with compounds of the formula VI is expediently carried out in an inert solvent in the presence of a base, such as specified above for the first preparation process, preferably in a temperature range from 100° to 190° C. The reaction is expediently carried out in the presence of an alkali metal iodide, such as, for example, sodium iodide or potassium iodide, if appropriate in an autoclave under pressure.

The reactions described above may expediently be carried out as a one-pot reaction, by initially reacting a compound of the formula IV with a compound of the formula III at 40° to 100° C. in the presence of a base in an inert solvent. A compound of the formula VI and, if appropriate, a further mole equivalent of a base, and an alkali metal iodide (for example potassium iodide) are subsequently added, without isolation of the compound of the formula V, and the mixture is heated to 100° to 190° C.

PREPARATION OF THE STARTING MATERIALS

Compounds of the formula IV in which E and E' have the meanings specified for E in the case of the formula II are known. They are prepared by converting a compound of the formula XII into a reactive ester group in a conventional fashion. Thus, for example, the compounds of the formula IV in which E' preferably denotes Cl or Br, and E denotes methanesulfonyloxy are prepared by reacting a compound of the formula XII in which Ar has the meanings specified in the case of the formula I and E' denotes Cl or Br with methanesulfonyl chloride at $-10°$ C. to $+50°$ C., expediently in an inert solvent, in the presence of a base. Compounds of the formula IV in which E, for example, denotes bromine are prepared by reaction of compounds of the formula XII

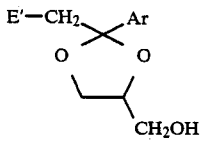

XII (E'=Cl or Br) with brominating agents, such as, for example $PBr_3$ or $POBr_3$, in an inert solvent at 0° C. to 100° C. Such compounds may also be prepared by reacting a compound of the formula XIII,

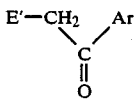

XIII in which E' denotes Cl or Br, and Ar has the specified meanings, with 1-bromo-2,3-propanediol in an inert solvent in the presence of strong acid with formation of a 1,3-dioxolane by methods which are known for such ketalizations. The compounds of the formula XII are known.

The process version (C), where a compound of the formula VII is reacted with a compound of the formula VIII with formation of a compound of the formula I, is generally carried out under the same conditions as for the preparation of compounds of the formula IV (version B). The ketalization of ketones of the formula VII using glycerole derivatives of the formula VIII is advantageously carried out in a mixture of solvents, comprising an inert solvent which forms an azeotropic mixture with water, such as, for example benzene, toluene, xylene, chlorobenzene or cyclohexane, and an alcohol, in the presence of a strong acid in a temperature range from 75° to 180° C. At least 1.5 equialents of a strong acid (relative to the azole compound of the formula VII) and as alcohols, aliphatic alcohols having a boiling point between 75° and 100° C. and/or monoethers of lower diols, boiling between 100° C. and 150° C., are advantageously used in this ketalization.

PREPARATION OF THE STARTING MATERIALS

The compounds of the formula VII are known and can be prepared by described methods.

Compounds of the formula VIII in which $R^1$, g, L, m, p, X, $R^2$ and n have the meanings specified in the case of the formula III and L, m and p do not simultaneously denote 0 and in which, preferably L and m simultaneously denote 0 are prepared by reacting compounds of the formula III with 1-halo-2,3-propanediol, in an analogous fashion to that described in Org. Synth. Collect. Vol. I, p. 296. In this connection, halogen denotes Cl, Br or I. Compounds of the formula VIII in which L, m and p simultaneously denote 0 and X, $R^2$ and n have the specified meanings are prepared by reacting glycerol with 2-chlolrobenzazoles of the formula XIa

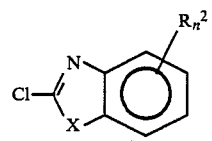

XIa in the presence of 1 equivalent of a base, expediently in an inert solvent. Those compounds of the formula VIII in which Z denotes S, and L, m and p simultaneously denote O are prepared by reacting 1-halo-2,3-propanediols with compounds of the formula III in which Z denotes S and L, m and p simultaneously denote O, advantageously in the presence of up to one equivalent of a base, expediently in an inert solvent.

In the process version (D), a compound of the formula IX is reacted either with a compound of the formula X in which E, m, p, X, $R^2$ and n have the specified meanings and, if p is 1, m preferably denotes 1, or with a compound of the formula XI in which Hal, X, $R^2$ and n have the specified meanings, expediently in an inert organic solvent in a temperature range from 0° to 180° C., preferably from 30° to 120° C. This reaction is advantageously carried out in the presence of a base, which is preferably used in an equimolar amount.

The synthesis of compounds of the formula I from the compounds of the formula IX, X or XI may alternatively be carried out without adding base. The reactants of the formulae IX and X or XI may be used in different molar ratios, i.e. in each case either the compounds of the formula IX or those of the formula X or XI may be employed in excess, but equimolar amounts are preferably used.

Suitable solvents are, for example, hydrocarbons, ethers in general, such as diethyl ether, 1,2-dimethoxyethane, tetrahydrofuran or dioxane, or acetonitrile, butyronitrile, dimethylformamide, dimethylacetamide, acetone, 4-methyl-2-pentanone, methylene chloride, chloroform, dimethyl sulfoxide, anisole, chlorobenzene or tetrachloroethylene, or mixtures of these solvents.

Suitable bases are those described as examples in the case of process version (A).

The reaction may likewise be carried out under the conditions of a phase-transfer reaction, as described in the description of the process version (A).

PREPARATION OF THE STARTING MATERIALS

Some of the compounds of the formula IX are known (cf. German Offenlegungsschrift No. 2,804,096, e.g. Example 21); those which have meanings for Ar which differ from those known and/or in which g denotes 1 or 2 may be prepared analogously to the known compounds (cf. German Offenlegungsschrift No. 2,804,096).

Some of the compounds of the formula X in which E, m, p, X, $R^2$ and n have the specified meanings are known. This applies particularly to compounds of the formula X where E=Cl.

In the compounds of the formula X, E preferably denotes Cl and, if p is 1, m preferably denotes 1. The compounds of the formula X where E=Cl or bromine are prepared by reacting an acyl chloride of the formula XIV,

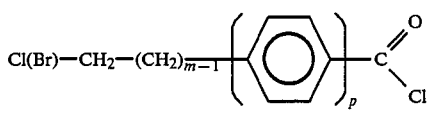

in which m and p have the specified meanings, with a compound of the formula XV,

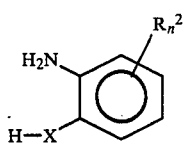

in which X, $R^2$ and n have the meanings specified in the case of the formula X, expediently in an inert organic solvent in a temperature range from 40°-180° C. The reaction here is advantageously carried out in an inert solvent which boils above 60° C. and which forms an azeotropic mixture with water and is thus suitable for the removal from the reaction mixture of water formed, such as, for example, benzene, chlorobenzene or toluene.

The compounds of the formula XI in which Hal, X, $R^2$ and n have the specified meanings are either known or may be prepared by known methods.

The process versions (E), where a compound of the formula IIa is reacted with a compound of the formula X, is expediently carried out in an inert, aprotic solvent in a temperature range from 30°-150° C., advantageously in an anhydrous medium in the presence of a base, which is preferably used in an equimolar amount.

Suitable solvents are, for example:

N,N-dimethylformamide, N,N-dimethylacetamide, dimethyl sulfoxide, N-methyl-2-pyrrolidone, dioxane, tetrahydrofuran, 1,2-dimethoxyethane, 4-methyl-2-pentanone or acetonitrile.

Mixtures of the solvents mentioned as examples may also be used.

Suitable bases are, for example, alkali metal amides, carbonates, hydroxides, alcoholates or hydrides, such as sodium carbonate, potassium carbonate, sodium hydroxide, sodium methylate, potassium t-butylate, sodium hydride or sodium amide, or organic bases, for example tertiary amines, such as triethylamine, tributylamine, ethylmorpholine or dimethylaminopyridine, or 1,5-diazabicyclo[5,4,0]undec-5-ene (DBU).

The reaction may likewise be carried out under the conditions of a phase-transfer reaction by allowing the reactants to act on one another in a suitable solvent, such as ether, dioxane, tetrahydrofuran, methylene chloride, N,N-dimethylformamide, N,N-dimethylacetamide, N-methyl-2-pyrrolidone, an aliphatic, cycloaliphatic or aromatic hydrocarbon, such as hexane, cyclohexane, benzene, toluene or xylene, anisole or chlorobenzene, with vigorous stirring in the presence of a phase-transfer catalyst and either a powdered alkali metal hydroxide, such as sodium hydroxide or potassium hydroxide, or a concentrated aqueous solution thereof, preferably in a temperature range from 40° to 150° C.

Suitable phase-transfer catalysts are, for example, trialkylbenzylammonium or tetraalkylammonium halides, hydroxides or hydrogen sulfates, preferably having 1 to 12 carbon atoms in the alkyl radical, or crown ethers, such as, for example, 12-crown-4, 15-crown-5, 18-crown-6 or dibenzo-18-crown-6.

The process version (F), where a compound of the formula IIa is reacted with a compound of the formula XI with formation of a compound of the formula I in which Z denotes O and A, Ar, $R^1$, g, X, $R^2$ and n have the specified meanings and L, m and p denote 0, is carried out under the same conditions, including those of a phase-transfer reaction, as described in the case of process version (E).

The compounds of the formulae IIa and XI are known or may be prepared analogously to the known compounds. Alkali metal alcoholates or alkaline-earth metal alcoholates of the formula IIa, in which M denotes such a metal atom, are likewise formed by known methods. The preferred process versions for the preparation of compounds of the formula I are A, B, D, E and F.

Depending on the process version and depending on the temperature range, the reaction times are a few minutes to several hours.

If necessary, the process products may be purified by recrystallization from a suitable solvent or mixture of solvents or by column chromatography on a silica gel.

The diastereomer racemates (cis or trans form) of the compounds of the formula I may be separated in a conventional fashion, for example by selective, fractional crystallization or by column chromatography.

Since the stereochemical configuration is already specified in the intermediate of the formula II the separation into the cis and trans form may be carried out as early as this stage, or even earlier, for example at the stage of the intermediates of the general formula IV, or in the case of the intermediates of the formula IX.

The cis- and trans-diastereomeric racemates may themselves be separated in a conventional fashion into their optical antipodes cis(+), cis(−), or trans(+) and trans(−).

The compounds I are preferably prepared by process versions A, B, D, E and F.

The invention furthermore relates to compounds of the formula IIIa,

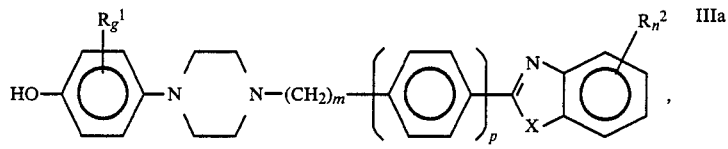

in which:
R¹ denotes $C_1$-$C_3$-alkyl, F or Cl,
g denotes 0, 1 or 2,
m denotes 0, 1, 2, 3 or 4,
p denotes 0 or, if m does not equal 0, denotes 0 or 1,
X denotes O or, if m does not equal 0 or if, simultaneously, m and p denote 0 and n does not equal 0, denotes O, S or N—R³, where
R³ denotes H, $C_1$-$C_4$-alkyl, phenyl or benzyl,
R², independently of one another, denote $C_1$-$C_4$-alkyl, $C_1$-$C_4$-alkoxy, F, Cl, Br, I, $SCH_3$, $CO$—$C_6H_5$, $CF_3$ or $NO_2$,
n denotes 0, 1 or 2, or if n is 2,
R², additionally, denotes a —CH=CH—CH=CH group which, together with the phenyl ring, forms a naphthyl radical,
or, if p is 0 and n is 1,
R², in addition, denotes a phenoxy group which is unsubstituted or substituted in the phenyl radical by up to 2 identical or different substituents, where the substitutents denote F, Cl, Br, $OCH_3$, $CH_3$ or $C_2H_5$,
and the acid-addition salts thereof.

Preferred compounds of the formula IIIa are those in which at least one of the substituents or indices has the following meaning:
R¹ denotes $CH_3$ or $C_2H_5$,
g denotes zero or 2,
m denotes zero, 1, 2 or 3,
p denotes zero or, if m does not equal zero, denotes zero or 1,
X denotes O or, if m is 1, 2 or 3, or m is zero and n is 1 or 2, denotes O or S,
R², independently of one another, denote $C_1$-$C_4$-n-alkyl, $OCH_3$, $OC_2H_5$, F, Cl, Br or, if, simultaneously p is 0 and n is 1, denotes $OC_6H_5$, and
n denotes zero, 1 or 2, and, if p is 1, m preferably denotes 1.

In this connection, the term "$C_1$-$C_4$-n-alkyl" is taken to mean a straight-chain alkyl radical having 1-4 carbon atoms.

Particularly preferred compounds of the formula IIIa are those in which at least one of the substituents or indices has the following meaning:
R¹ denotes $CH_3$,
g denotes zero or 2,
m denotes zero, 1, 2 or 3,
p denotes zero or, if m does not equal zero, denotes zero or 1,
X denotes O or, if m is 1, 2 or 3, denotes O or S,
R², independently of one another, denote $CH_3$, $C_2H_5$, $OCH_3$, $OC_2H_5$, Cl or Br,
n denotes zero, 1 or 2, and
if p is 1, m preferably denotes 1.

The compounds of the formula IIIa in which R¹, g, m, p, X, R² and n have the specified meanings are new and represent valuable intermediates for the preparation of the compounds of the formula I which have a strong antimycotic and fungicidal action. Some of the compounds of the formula IIIa likewise have an antimycotic or fungicidal action. In addition, some of the compounds of the formula IIIa exhibit actions on the cardiovascular system.

In addition, the invention relates to a process for the preparation of compounds of the formula IIIa, wherein a compound of the formula XVI,

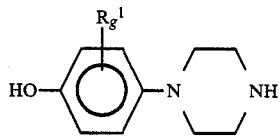

in which R¹ and g have the meanings specified in the case of the formula IIIa, or a salt of this compound, is reacted either with a compound of the formula X,

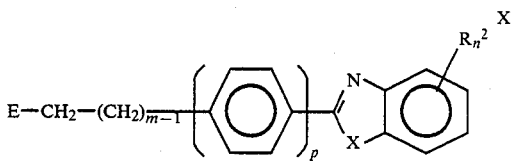

in which
E denotes Cl, Br, I, acyloxy, such as acetoxy, trifluoroacetoxy, benzoyloxy, nitrobenzoyloxy, $C_1$-$C_3$-alkylsulfonyloxy, such as methanesulfonyloxy, or arylsulfonyloxy, such as benzene-, nitrobenzene-, bromobenzene- or toluenesulfonyloxy,
m denotes 1, 2, 3 or 4, and
p, X, R² and n have the meanings specified in the case of the formula IIIa,
or with a compound of the formula XI

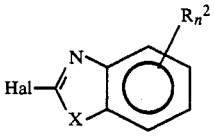

in which
Hal denotes Cl, Br or I, preferably Cl,
X denotes O, or, if n does not equal zero, denotes O, S or N—R³, where R³ denotes H, $C_1$-$C_4$-alkyl, phenyl or benzyl, and
R² and n have the meanings specified in the case of the formula IIIa,
and, if appropriate, the compounds of the formula IIIa obtained are converted into their acid-addition salts with inorganic or organic acids.

For the reaction, according to the invention, with a compound of the formula XVI, either a compound of the formula X in which E denotes Cl, Br or I, m denotes 1, 2 or 3, p denotes zero or 1, X denotes O or S, $R^2$ independently of one another, denote $C_1$-$C_4$-n-alkyl, $OCH_3$, $OC_2H_5$, F, Cl, Br, or, if p is zero and n is 1, denote $OC_6H_5$, and n denotes zero, 1 or 2, or a compound of the formula XI in which Hal denotes Cl, X denotes O or, if n does not equal zero, denotes O or S, $R^2$, independently of one another, denote $C_1$-$C_4$-n-alkyl, $OCH_3$, $OC_2H_5$, F, Cl, Br, or, if n is 1, denote $OC_6H_5$, and n denotes zero, 1 or 2, are preferred.

The process, according to the invention, for the preparation of compounds of the formula IIIa is expediently carried out in an inert organic solvent in a temperature range from 0° to 180° C., preferably from 30° to 120° C., advantageously in the presence of a base, which is preferably employed in an equivalent amount. If salts of the compound of the formula XVI are used for the process, the stoichiometric amount of base corresponding to the amount of salt is added. If desired, a further proportion of base may then be used in addition.

The synthesis of compounds of the formula IIIa from the compounds of the formulae XVI and X or XI may also be carried out without adding base, so long as the compounds XVI are not used as the salt. The reactants of the formulae XVI and X or XI may be used in different molar ratios, i.e. in each case either the compounds of the formula XVI or those of the formula X or XI may be used in excess, but equimolar amounts are advantageously used.

Suitable solvents are, for example, hydrocarbons, ethers in general, such as diethyl ether, 1,2-dimethoxyethane, tetrahydrofuran or dioxane, or acetonitrile, butyronitrile, dimethylformamide, dimethylacetamide, acetone, 4-methyl-2-pentanone, methylene chloride, chloroform, dimethyl sulfoxide, anisole, chlorobenzene or tetrachloroethylene, or mixtures of these solvents.

Suitable bases are those mentioned as examples in the case of process version (A).

Depending on the temperature range, the reaction times are a few minutes to several hours.

If necessary, the process products may be purified by recrystallization from a suitable solvent or mixture of solvents or by column chromatography on silica gel.

Preparation of the starting materials:

The compound of the formula XVI where g=0 is known. Compounds of the formula XVI in which g denotes 1 or 2 and $R^1$ has the meanings specified in the case of the formula I are prepared, analogously to the known compounds, by reaction of appropriate 4-methoxyanilines with bis-(2-chloroethyl)amine and subsequent cleavage of the phenol ether using concentrated aqueous hydrobromic acid. The preparation of the compounds of the formula X and XI in which E, m, p, X, $R^2$, n and Hal have the specified meanings has already been described in the preparation of the starting materials for the process version (D) for the preparation of compounds of the formula I.

The compounds of the formula I and their acid-addition salts are valuable medicaments. In particular, they have an antimicrobial action and are suitable for the prevention and treatmemnt of fungal infections in humans and in various types of mammal.

In vitro, the new compounds have a very good action against dermatophytes, such as, for example, *Trichophyton mentagrophytes, Microsporum canis* and *Epidermophyton floccosum;* against mold fungi, such as, for example, *Aspergillus niger,* or against yeasts, such as, for example, *Candida albicans, C. tropicalis, Torulopsis glabrata* and *Trichosporon cutaneum,* or against protozoa, such as *Trichomonas vaginalis* or *T. fetus,* or against Gram-positive and Gram-negative bacteria.

After oral or parenteral administration, the compounds also have a very good systemic effect in vivo, for example against *Candida albicans,* for example in experimental kidney candidiasis of the mouse. There is likewise a very good effect against various pathogens of dermatomycosis (for example *Trichophyton mentagrophytes*) in guinea pigs after oral, parenteral or, in particular, local administration.

Those compounds of the formula I in which L, m and p denote zero, Z denotes O or S, and A, Ar, X, $R^2$ and n have the specified meanings are particularly suitable for local administration, whereas those in which L, m and p, particularly L and m, do not equal zero, within context of the specified meanings, may be used for oral and parenteral administration as well as for local administration.

The following may be mentioned as examples of areas of indication in human medicine:

Dermatomycosis and a systemic mycosis caused by *Trichophyton mentagrophytes* and other Trichophyton species, Microsporon species, *Epidermophyton floccosum,* blastomycetes, biphasic fungi and mold fungi.

The following may be mentioned as examples of areas of indication in veterinary medicine:

All dermatomycoses and systemic mycoses, particularly those which are caused by the abovementioned pathogens.

The present invention includes pharmaceutical preparations, which, beside nontoxic, inert pharmaceutically suitable excipients, contain one or more active compounds according to the invention or which comprise one or more active compounds according to the invention, and also processes for the preparation of these preparations.

Nontoxic, inert pharmaceutically acceptable excipients are taken to mean solid, semisolid or liquid diluents, fillers and formulation auxiliaries of all types.

Suitable forms of administration are, for example, tablets, dragees, capsules, pills, aqueous solutions, suspensions, and emulsions, if appropriate sterile injectable solutions, nonaqueous emulsions, suspensions and solutions, ointments, creams, pastes, lotions, sprays etc.

The therapeutically active compounds should expediently be present in the abovementioned pharmaceutical preparations in a concentration from about 0.01 to 99.0 percent, preferably from about 0.05 to 50% by weight of the total mixture.

The abovementioned pharmaceutical preparations may also contain further pharmaceutical active compounds in addition to the active compounds according to the invention.

The abovementioned pharmaceutical preparations are prepared in a conventional fashion by known methods, for example by mixing the active compound(s) with the excipient(s).

The present invention also includes the use of the active compounds according to the invention and the use of pharmaceutical preparations which contain one or more active compounds according to the invention, in human and veterinary medicine for the prevention, improvement and/or cure of the abovementioned disorders.

The active compounds of the pharmaceutical preparations may be administered locally, orally, parenterally, intraperitoneally and/or rectally.

In order to achieve the desired results, it has generally proven expedient, both in human and in veterinary medicine, to administer the active compound or compounds according to the invention in total amounts of at least about 0.05, preferably 0.1, in particular 0.5 mg and at most 200, preferably 100, in particular 30 mg/kg of bodyweight per 24 hours, if appropriate in the form of several individual doses. The total amount is administered in 1 to 8, preferably in 1 to 3, individual doses.

However, it may be necessary to deviate from the dosages mentioned, and in particular to do so as a function of the species and the bodyweight of the object to be treated, the nature and severity of the disorder, the type of the preparation and the administration of the medicaments, and the period of time or interval over which the administration is effected. Thus, it may in some cases be sufficient to manage with less than the abovementioned amount of active compound, whereas in other case, it is necessary to exceed the abovementioned amount of active compound. The optimum dosage necessary and the type of administration of the active compounds can in each case easily be determined by any expert on the basis of his expert knowledge.

The new compounds of the formula I are also suitable for the treatment of protozooses in humans and animals as is caused, for example, by infections by *Trichomonas vaginalis, Entamoeba histolytica, Trypanosoma cruzi* and *Leishmania donovani.*

The new compounds may be administered orally or locally. Oral administration is carried out in pharmaceutically conventional preparations, for example in the form of tablets or capsules.

The novel compounds of the formula I are also active as biocides. They are distinguished, in particular, by their fungicidal activity in the case of phytopathogenic fungi. Even the fungal pathogens which have already penetrated into the vegetative tissue can be combated successfully. This is particularly important and advantageous in those fungal diseases which, once the infection has occurred, cannot be combated effectively using the fungicides which are otherwise conventional. The range of action of the new compounds covers a large number of different phytopathogenic fungi, such as, for example, *Piricularia oryzae, Plasmopara viticola,* various types of rust, but above all *Venturia inaequlis, Cercospora beticola* and true mildew fungi in fruit, vegetable, cereal and ornamental plant growing.

The new compounds of the formula I are furthermore suitable for use in industrial area, for example as wood-protection agents, as preservatives in paints, in cooling lubricants for metal working, or as preservatives in drilling and cutting oils.

The new compounds may be used in the conventional preparations as wettable powders, emulsifiable concentrates, sprayable solutions, powders, dressing agents, dispersions, granules or microgranules.

The following examples serve to illustrate the invention in greater detail, without limiting it.

EXAMPLES OF THE PREPARATION PROCESS VERSION (F)

EXAMPLE 1

0.43 g (14.4 mmol) of 80% strength sodium hydride/oil dispersion was added to a solution of 3.95 g (12 mmol) of 2-S,(R)-(2,4-dichlorophenyl)-2-(imidazol-1-ylmethyl)-4-R,(S)-hydroxymethyl-1,3-dioxolane (cis form) in 36 ml of absolute N,N-dimethylformamide (DMF). The mixture was stirred for 30 minutes at about 45° C., the evolution of hydrogen subsiding. A solution of 2.15 g (14 mmol) of 2-chlorobenzoxazole in 3 ml of absolute DMF was then added dropwise over 5 minutes, and the mixture was stirred for a further 17 hours at 70° C. The DMF was subsequently removed by distillation in vacuo (3–8 mbar). 50 ml of water and 50 ml of $CH_2Cl_2$ were added to the residue, the mixture was shaken thoroughly, the phases were separated, and the aqueous phase was extracted a further three times with $CH_2Cl_2$. The combined $CH_2Cl_2$ extracts were dried using $Na_2SO_4$, filtered and evaporated in vacuo. The residue, 6.4 g of a viscous oil, was chromatographed on a silica gel/$CH_2Cl_2$ column (diameter 2.6 cm, height 30 cm). Silica gel S, Riedel-de Haen, particle size 0.063–0.2 mm, was used. Elution was carried out in fractions using $CH_2Cl_2$, and the fractions were examined by thin-layer chromatography (TLC) (prepared TLC plates, silica gel 60, F 254, Merck). In this fashion, 4.6 g of 2-S,(R)-(2,4-dichlorophenyl)-2-(imidazol-1-ylmethyl)-4-R,(S)-(benzoxazol-2-yloxymethyl)-1,3-dioxolane, virtually pure according to thin-layer chromatography, were obtained as a viscous oil (yield≐85%).

Elemental analysis: $C_{21}H_{17}Cl_2N_3O_4$ (MW 446.31) calc. C 56.52, H 3.48, N 9.42, found C 56.1, H 3.8, N 9.1%; the expected structure is confirmed by the $^1H$ NMR spectrum ($CDCl_3$).

Nitrate formation: 2.23 g (5 mmol) of the viscous oily compound obtained above were dissolved in a mixture of 10 ml of ethyl acetate and 15 ml of ether, and 5 ml of a 1 m $HNO_3$/ethyl acetate solution were added with stirring. A crystallined precipitate (nitrate) was produced during this.

Ether was added portionwise until turbidity of the solution no longer occurred, the crystals were filtered off under suction and washed with ether, and the crystalline product was dried. 2.04 g of 2-S,(R)-(2,4-dichlorophenyl)-2-imidazol-1-ylmethyl)-4-R,(S)-(benzoxazol-2-yloxymethyl)-1,3-dioxolane nitrate, melting point 141°–142° C., were obtained;

Elemental analysis: $C_{21}H_{18}Cl_2N_4O_7$ (MW 509.32) calc. C 49.52, H 3.56, Cl 13.92, N 11.00, found C 48.7, H 3.7, Cl 13.7, N 10.7%.

With principally the same procedure as described above, dimethyl sulfoxide, N,N-dimethylacetamide or N-methyl-2-pyrrolidone, and mixtures of these solvents with, for example, tetrahydrofuran, dioxane, 1,2-dimethoxyethane or acetonitrile, may also be used.

EXAMPLE 2

The following compounds of the formula I (L, m and p always simultaneously denote zero, Z=0) shown in Table 1 were prepared according to Example 1, in each case using the appropriate compound of the formula IIa (A=CH or N, Ar=2,4-dichlorophenyl and M=H) and the appropriate compounds of the formula XIa. The radicals and indices A, X, $R^2$ and n, which are different in each case, can be seen from Table 1.

analysis: $C_{21}H_{17}Cl_2N_3O_2S_2$ (MW 478.44), calc. C. 52.72, H 3.58, N 8.78, S 13.40; found C 52.1, H 3.5, N 8.6, S 13.1.

TABLE 1

IIa (M = H) + XIa → I (L, m, p = O, Z = O)

| Comp. No. | A | X | $R^2$ | n | Base | m.p. [°C] | Analysis % Calc. | Analysis % Found | Salt | m.p. [°C] | Analysis % Calc. | Analysis % Found | 2,4-isomers* |
|---|---|---|---|---|---|---|---|---|---|---|---|---|---|
| 1.1 | CH | O | 6-Cl | 1 | Base | 148–50 | C 52.47 H 3.36 N 8.74 | 52.7 3.4 8.8 | Nitrate | 162–63 | C 46.39 H 3.15 N 10.30 | 46.4 3.4 10.1 | cis |
| 1.2 | N | O | — | 0 | Base | 126–27 | C 53.71 H 3.61 N 12.53 | 53.3 3.3 12.7 | — | | | | cis |
| 1.3 | CH | O | 5.6-$(CH_3)_2$— | 2 | Base | 136–37 | C 58.24 H 4.46 N 8.86 | 57.9 4.3 8.6 | — | | | | cis |
| 1.4 | CH | S | — | 0 | Base | | C 54.55 H 3.71 N 9.09 | 54.2 3.8 9.2 | Nitrate | 127–28 | C 48.01 H 3.45 N 10.66 | 48.4 3.7 10.6 | cis |
| 1.5 | CH | S | 6-Cl | 1 | Base | | C 50.77 H 3.25 N 8.46 | 49.9 3.4 8.4 | Nitrate | 189–90 | C 45.05 H 3.06 N 10.01 | 45.1 3.3 9.7 | cis |
| 1.6 | N | S | 6-Cl | 1 | Base | 131–32 | C 48.26 H 3.04 N 11.26 | 48.4 3.3 11.1 | — | | | | cis |
| 1.7 | CH | S | 6-$OC_2H_5$ | 1 | Base | | C 54.54 H 4.18 N 8.30 | 53.8 4.3 8.3 | Nitrate | 189–90 | C 48.51 H 3.89 N 9.84 | 48.6 4.1 9.3 | cis |
| 1.8 | CH | N—$CH_3$— | | 0 | Base | | C 57.53 H 4.39 N 12.20 | 56.7 4.4 12.0 | — | | | | cis |

*Cis and trans refer to the azolylmethyl radical and to the (substituted) oxymethyl radical in the 2 or 4 position respectively of the dioxolane ring.

EXAMPLES OF THE PREPARATION PROCESS VERSION (A)

EXAMPLE 3

0.330 g (11 mmol) of 80% strenght sodium hydride/oil dispersion was added to a solution of 1.84 g (11 mmol) of 2-mercaptobenzothiazole in 25 ml of absolute DMF. When the evolution of hydrogen had subsided, a solution of 4.07 g (10 mmol) of 2-S,(R)-(2,4-dichlorophenyl)-2-(imidazol-1-ylmethyl)-4-R,(S)-methanesulfonyloxymethyl-1,3-dioxolane in 13 ml of absolute DMF was added, and the mixture was stirred for a further 8 hours at 90° C. The DMF was then stripped off in vacuo in a rotary evaporator, and 30 ml of water and 40 ml of $CH_2Cl_2$ were added to the residue, and the mixture was shaken thoroughly. After separating the phases, the aqueous phase was extracted a further twice with $CH_2Cl_2$. The combined $CH_2Cl_2$ extracts were dried, filtered and evaporated in vacuo. The residue was chromatographed on a silica gel (silica gel S, Riedel-de Haen, 0.063–0.2 mm)/$CH_2Cl_2$ column, in analogous fashion to that described in Example 1. The fractions which were unary according to TLC were combined and freed from solvent in vacuo. 4.03 g (84% of theory) of 2-S,(R)-(2,4-dichlorophenyl)-2-(imidazol-1-ylmethyl)-4-R,(S)-(benzothiazol-2-ylthiomethyl)-1,3-dioxolane were obtained as a viscous oil,

EXAMPLE 3

A solution of 4.07 g (10 mmol) of cis-2-(2,4-dichlorophenyl)-2-(imidazol-1-ylmethyl)-4-methanesulfonyloxymethyl-1,3-dioxolane, 2.0 g (13 mmol) of 2-mercaptobenzothiazole and 1.5 g (15 mmol) of triethylamine in 25 ml of acetonitrile was refluxed for 16 hours. The solvent was subsequently stripped off in vacuo in a rotary evaporator, and the residue remaining was worked up as described in Example 3 and chromatographed on silica gel S. 4.3 g (90% of theory) of 2-S(R)-(2,4-dichlorophenyl)-2-(imidazol-1-ylmethyl)-4-R,(S)-benzothiazol-2-ylthiomethyl)-1,3-dioxolane were obtained as a viscous oil (the $^1H$ NMR spectrum and the TLC behaviour are identical to the substance obtained according to Example 3).

EXAMPLE 5

The following compounds of the formula I (Z=S, L, m and p=0) shown in Table 2 were prepared according to Example 3, in each case using the methanesulfonates IIb or IIc (cf. Table 2) and the appropriate compounds of the formula IIIb (M=H, Z=S, L, m and p=0).

TABLE 2

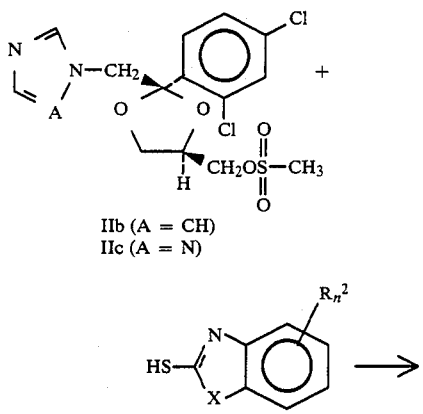

IIb (A = CH)
IIc (A = N)

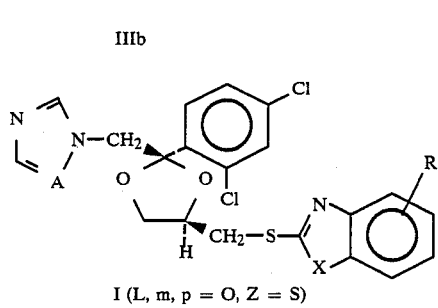

IIIb

I (L, m, p = O, Z = S)

| Comp. No. | A | X | R² | n | Analysis % Calc. | Found | 2,4-isomers |
|---|---|---|---|---|---|---|---|
| 2.1 | CH | O | — | 0 | C 54.55<br>H 3.71<br>N 9.09<br>S 6.94 | 53.9<br>3.7<br>8.9<br>7.2 | cis |
| 2.2 | N | O | — | 0 | C 51.84<br>H 3.48<br>N 12.09<br>S 6.92 | 51.9<br>3.4<br>12.0<br>7.0 | cis |
| 2.3 | CH | S | 7-CO—C₆H₅ | 1 | C 57.73<br>H 3.63<br>N 7.21 | 57.1<br>3.8<br>7.2 | cis |
| 2.4 | CH | S | 7-COOCH₃ | 1 | C 51.49<br>H 3.57<br>N 7.83 | 50.8<br>3.65<br>7.75 | cis |
| 2.5 | CH | S | 7-Cl | 1 | C 49.18<br>H 3.14<br>N 8.19 | 49.0<br>3.2<br>8.1 | cis |
| 2.6 | CH | S | 6-CH₃ | 1 | C 53.66<br>H 3.89<br>N 8.53 | 53.4<br>3.9<br>8.4 | cis |
| 2.7 | CH | S | 6-OC₄H₉ | 1 | C 54.54<br>H 4.58<br>N 7.63<br>S 11.65 | 53.6<br>4.5<br>7.3<br>11.5 | cis |
| 2.8 | CH | N—CH₃— | | 0 | C 55.58<br>H 4.24<br>N 11.79 | 55.2<br>4.4<br>11.5 | cis |

EXAMPLES OF THE PREPARATION PROCESS—VERSION (E)

EXAMPLE 6

0.34 g (11.3 mmol) of 80% strength sodium hydride/oil dispersion was added to a solution of 3.29 g (10 mmol) of cis-2-(2,4-dichlorophenyl)-2-(imidazol-1-ylmethyl)-4-hydroxymethyl-1,3-dioxolane in 40 ml of absolute DMF. After stirring for 25 minutes at 40° C., after which the evolution of H₂ had subsided, a solution of 1.85 g (11 mmol) of 2-chloromethylbenzoxazole in 7 ml of absolute DMF was added dropwise at 40° C., and the mixture was stirred for a further 2.5 hours at 50° C. After removing the DMF by distillation in vacuo in a rotary evaporator, the residue remaining was further worked up as described in Example 1. The residue from the methylene chloride extract was chromatographed on a silica gel S (0.063–0.2 mm, diameter 2.6 cm, height 36 cm)-CH₂Cl₂ column. Elution was carried out in fractions using CH₂Cl₂ and CH₂Cl₂/C₂H₅OH mixtures. The fractions which were unary in the TLC were combined and evaporated in vacuo. 1.26 g (27.4% of theory) of pure 2-S,(R)-(2,4-dichlorophenyl)-2-(imidazol-1-ylmethyl)-4-R,(S)-[(benzoxazol-2-ylmethyloxy)methyl]-1,3-dioxolane were produced as a highly viscous oil, analysis: C₂₂H₁₉Cl₂N₃O₄ (MW 460.33), calc. C 57.40, H 4.16, N 9,13, found C 56.8, H 4.4, N 8.8%; the structure was confirmed by the ¹H NMR spectrum (CDCl₃).

EXAMPLE 7

By the same procedure as described in Example 6, starting from 2-chloromethylbenzothiazole in place of 2-chloromethylbenzoxazole, cis-2-(2,4-dichlorophenyl)-2-(imidazol-1-ylmethyl)-4-[benzothiazol-2-ylmethyloxy)methyl]-1,3-dioxolane was obtained as a viscous oil in a yield of 17%, analysis: C₂₂H₁₉Cl₂N₃O₃S (MW 476.40) calc. C 55.47, H 4.02, N 8.82; found C 55.3, H 4.3, N 8.6%.

EXAMPLE 8

By the same procedure as described in Example 6, starting from 2-chloromethyl-6-chlorobenzothiazole and cis-2-(4-chlorophenyl)-2-(imidazol-1-ylmethyl)-4-hydroxymethyl-1,3-dioxolane, cis-2-(4-chlorophenyl)-2-(imidazol-1-ylmethyl)-4-[(6-chlorobenzothiazol-2-ylmethoxyloxy)methyl]-1,3-dioxolane was obtained as a viscous oil in a yield of 19%, analysis: C₂₂H₁₉Cl₂N₃O₃S (MW 476.40) calc. C 55.47, H 4.02, N 8.82, S 6.73; found C 55.0, H 3.8, N 8.7, S 6.6%.

EXAMPLE 9

0.55 g (18.2 mmol) of an 80% strength NaH/oil dispersion was added to a solution of 4.9 g (15 mmol) of cis-2-(2,4-dichlorophenyl)-2-(imidazol-1-ylmethyl)-4-hydroxymethyl-1,3-dioxolane in 50 ml of absolute N,N-dimethylformamide (DMF). The mixture was stirred for 40 minutes at 40° C., 5.25 g (18.2 mmol) of 2-(4-bromomethylphenyl)benzoxazole were then added, and the mixture was stirred for a further 16 hours at 80° C. Work-up was subsequently effected as described in Example 1. The residue from the CH₂Cl₂ extract (8.4 g of a viscous oil) was chromatographed as described in Example 6 on a silica gel S/CH₂Cl₂ diameter 2.6 cm, height 37 cm) column. After evaporation of the solvent in vacuo, 4.38 g (54.5% of theory) of crystalline, pure cis-2-(2,4-dichlorophenyl)-2-(imidazol-1-ylmethyl)-4-[(4-(benzoxazol-2-yl)benzyl)oxymethyl]-1,3-dioxolane were obtained as fractions which were unary according to TLC. The substance may be recrystallized from methanol (melting point 111°–112° C.);

analysis: C₂₈H₂₃Cl₂N₃O₄ (MW 536.43) calc. C 62.69, H 4.32, N 7.83; found C 62.4, H 4.4, N 7.6. Nitrate formation: 1.93 g (3.6 mmol) of base were dissolved in 15 ml of ethyl acetate, and 3.6 ml of 1M HNO₃/ethyl acetate were added with stirring. Ether was subsequently added until no further precipitate was produced, and the precipitate was filtered off under suction. 2.05 g (yield of nitrate, 95.3% of theory) of cis-2-

(2,4-dichlorophenyl)-2-(imidazol-1-ylmethyl)-4-[4-(benzoxazol-2-yl)benzyl)oxymethyl]-1,3-dioxolane nitrate were obtained; melting point 121°–2° C., analysis: $C_{28}H_{24}Cl_2N_4O_7$ (MW 599.45) calc. C 56.10, H 4.04, N 9.35; found C 55.5, H 4.0, N 9.2%.

EXAMPLE 10

The following were prepared according to the procedure described in Example 9: Cis-2-(2,4-dichlorophenyl)-2-(imidazol-1-ylmethyl)-4-[(4-(5-chlorobenzoxazol-2-yl)benzyl)oxymethyl]-1,3-dioxolane, melting point 122°–23° C., analysis: $C_{28}H_{22}Cl_3N_3O_4$ (MW 570.88), calc.: C 58.91, H 3.88, N 7.36; found C 58.1, H 3.9, N 7.3%.

Cis-2-(2,4-dichlorophenyl)-2-(imidazol-1-ylmethyl)-4-[(4-(benzothiazol-2-yl)benzyl)oxymethyl]-1,3-dioxolane, analysis: $C_{28}H_{23}Cl_2N_3O_3S$ (MW 552.50), calc. C 60.87, H 4.20, N 7.61; found C 60.2, H 3.8, N 7.5%.

Cis-(4-fluorophenyl)-2-(1,2,4-triazol-1-ylmethyl)-4-[(4-(benzothiazol-2-yl)benzyl)oxymethyl]-1,3-dioxolane, melting point 108°–9° C., analysis: $C_{27}H_{23}FN_4O_3S$ (MW 502.58), calc. C 64.53, H 4.61, N 11.15, S 6.38; found C 64.1, H 4.7, N 11.3, S 6.0%.

FURTHER EXAMPLES OF THE PREPARATION PROCESS—VERSION (A)

EXAMPLE 11

0.33 g (11 mmol) of an 80% strength NaH/oil dispersion was added in portions to a solution of 2.11 g (10 mmol) of 2-(4-hydroxyphenyl)benzoxazole in 50 ml of absolute DMF at 16°–35° C. When the evolution of hydrogen had subsided, 4.07 g (10 mmol) of cis-2-(2,4-dichlorophenyl)-2-(imidazol-1-ylmethyl)-4-methanesulfonyloxymethyl-1,3-dioxolane were added, and the mixture was stirred for 7 hours at 75° C. About 60% of the DMF were then removed by distillation in vacuo in a rotary evaporator. About 50 ml of water were added to the residue with stirring and cooling. A crystalline precipitate was produced during this. After stirring for a further 1 hour at 2°–6° C., the crystalline product was filtered off under suction, dried in vacuo and recrystallized from ethyl acetate. 3.2 g (61.3% of theory) of pure cis-2-(2,4-dichlorophenyl)-2-(imidazol-1-ylmethyl)-4-[(4-benzoxazol-2-yl)phenoxy)methyl]-1,3-dioxolane, melting point 170°–71° C., were obtained in this procedure, analysis: $C_{27}H_{21}Cl_2N_3O_4$ (MW 522.40), calc. C 62.08, H 4.05, N 8.04; found C 61.6, H 4.0, N 7.9%.

By the same procedure, starting from the same methanesulfonate and 5-chloro-2-(4-hydroxyphenyl)benzoxazole, pure cis-2-(2,4-dichlorophenyl)-2-(imidazol-1-ylmethyl)-4-[(4-(5-chlorobenzoxazol-2-yl)phenoxy)methyl]-1,3-dioxolane, melting point 196°–7° C., were obtained in a yield of 63%.

analysis: $C_{27}H_{20}Cl_3N_3O_4$ (MW 556.85), calc. C 58.24, H 3.62, N 7.55; found C 57.8, H 3.7, N 7.4%.

EXAMPLE 12

154 mg (5.13 mmol) of an 80% strength sodium hydride/oil dispersion were added to a solution of 1.48 g (5 mmol) of 2-(4-(4-hydroxyphenyl)piperazin-1-yl)benzoxazole (cf. Example 29) in 20 ml of absolute N,N-dimethylformamide (DMF) at room temperature. When the evolution of hydrogen was complete, a solution of 2-S,(R)-(2,4-dichlorophenyl)-2-(imidazol-1-ylmethyl)-4(R),(S)-methanesulfonyloxymethyl-1,3-dioxolane (cis form) in 15 ml of absolute DMF was added dropwise, and the mixture was stirred for 4.5 hours at 100° C. The DMF was subsequently removed by distillation in vacuo (4–16 mbar) in a rotary evaporator, and $CH_2Cl_2$ and water were added to the residue remaining and shaken thoroughly. The pH of the aqueous phase was adjusted to about 6 using dilute HCl. After separating the phases, the aqueous phase was extracted a further twice with $CH_2Cl_2$. The combined methylene chloride extracts were dried using $Na_2SO_4$, filtered and evaporated in vacuo. The crystalline residue remaining was recrystallized from acetonitrile. 1.75 g (57.7% of theory) of pure 2-S,(R)-(2,4-dichlorophenyl)-2-(imidazol-1-ylmethyl)-4-R,(S)-[4-(4-(benzoxazol-2-yl)piperazin-1-yl)phenoxymethyl]-1,3-dioxolane, melting point 169°–70° C., were obtained; analysis: $C_{31}H_{29}Cl_2N_5O_4$ (MW 606.53), calc. C 61.39, H 4.82, Cl 11.69, N 11.55; found 60.7, H 4.8, Cl 12.0, N 11.3%.

EXAMPLE 13

The compounds of the formula Ia shown in Table 3 were prepared by process version A) by the same procedure as described in Example 12, using 2-S,(R)-(2,4-dichlorophenyl)-2-(imidazol-1-ylmethyl)- or -(1,2,4-triazol-1-ylmethyl)-4-R,(S)-methanesulfonyloxymethyl-1,3-dioxolane (IIb and IIc respectively) and in each case the appropriate 4-(4-hydroxyphenyl)piperazin-1-yl derivative of the formula IIIc (M=H, Z=O, L=1 and m and p=0).

TABLE 3
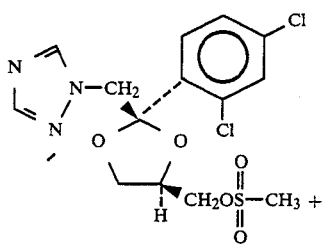
IIb (A = CH)
IIc (A = N)
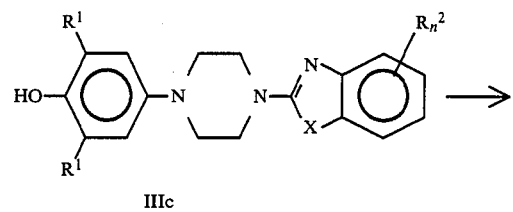
IIIc
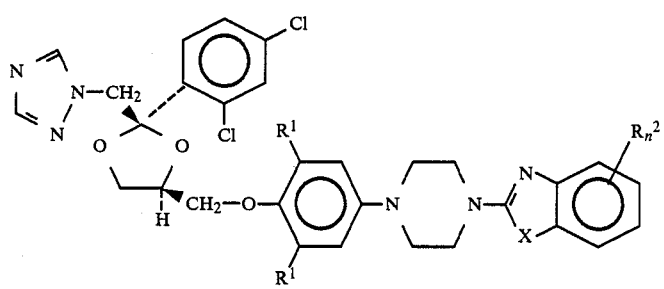
Ia (m, p = O, Z = O)
| Comp. No. | A | R¹ | X | R² | n | | Analysis % Calc. | Found | m.p. [°C.] |
|---|---|---|---|---|---|---|---|---|---|
| 3.1 | N | H | O | — | 0 | C | 59.31 | 59.5 | 172–3 |
|  |  |  |  |  |  | H | 4.65 | 4.6 |  |
|  |  |  |  |  |  | N | 13.83 | 13.7 |  |
| 3.2 | CH | H | O | 6-Cl | 1 | C | 58.09 | 57.9 | 144–5 |
|  |  |  |  |  |  | H | 4.40 | 4.3 |  |
|  |  |  |  |  |  | N | 10.93 | 10.9 |  |
| 3.3 | N | H | O | 6-Cl | 1 | C | 56.13 | 55.9 | 139–40 |
|  |  |  |  |  |  | H | 4.24 | 4.1 |  |
|  |  |  |  |  |  | N | 13.09 | 13.0 |  |
| 3.4 | CH | H | O | 5-CH$_3$ | 1 | C | 61.93 | 6.18 | 173–4 |
|  |  |  |  |  |  | H | 4.90 | 5.0 |  |
|  |  |  |  |  |  | N | 11.29 | 11.0 |  |
| 3.5 | CH | H | S | 6-Cl | 1 | C | 56.67 | 56.2 | 121–2 |
|  |  |  |  |  |  | H | 4.30 | 4.7 |  |
|  |  |  |  |  |  | N | 10.66 | 10.4 |  |
| 3.6 | N | H | S | 6-Cl | 1 | C | 54.76 | 54.0 | 146–7 |
|  |  |  |  |  |  | H | 4.14 | 4.1 |  |
|  |  |  |  |  |  | N | 12.77 | 12.3 |  |
| 3.7 | CH | H | S | 6-OC$_2$H$_5$ | 1 | C | 59.46 | 59.2 | 172–3 |
|  |  |  |  |  |  | H | 4.99 | 5.0 |  |
|  |  |  |  |  |  | N | 10.51 | 10.3 |  |
| 3.8 | N | H | S | 6-OC$_2$H$_5$ | 1 | C | 57.57 | 57.5 | 173–4 |
|  |  |  |  |  |  | H | 4.83 | 4.8 |  |
|  |  |  |  |  |  | N | 12.59 | 12.2 |  |
| 3.9 | CH | CH$_3$ | O | 5-CH$_3$ | 1 | C | 62.96 | 62.6 | 160–1 |
|  |  |  |  |  |  | H | 5.44 | 5.4 |  |
|  |  |  |  |  |  | N | 10.80 | 10.6 |  |
| 3.10 | N | CH$_3$ | O | 5-CH$_3$ | 1 | C | 61.01 | 61.2 | — |
|  |  |  |  |  |  | H | 5.28 | 5.3 |  |
|  |  |  |  |  |  | N | 12.94 | 12.6 |  |
| 3.11 | CH | CH$_3$ | S | 5-Cl 6-CH$_3$ | 2 | C | 58.41 | 58.6 | — |
|  |  |  |  |  |  | H | 4.90 | 4.9 |  |
|  |  |  |  |  |  | N | 10.02 | 9.8 |  |
|  |  |  |  |  |  | S | 4.59 | 4.7 |  |

EXAMPLE 14

370 mg (12.31 mmol) of an 80% strength NaH/oil dispersion were added to a solution of 3.71 g (12 mmol) of 1-(4-hydroxyphenyl)-4-(benzoxazol-2-ylmethyl)piperazine in 45 ml of absolute DMF, and, when the $H_2$ evolution was complete, a solution of 5.0 g of cis-2-(2,4-dichlorophenyl)-2-(imidazol-1-ylmethyl)-4-methanesulfonyloxymethyl-1,3-dioxolane (IIb) in 35 ml of absolute DMF was subsequently added, and the mixture was stirred for 3 hours at 95° C. The subsequent work-up was carried out in the fashion described in Example 12. The residue from the methylene chloride extract (8.5 g) was chromatographed on a silica gel S/CH$_2$Cl$_2$ column (diameter 2.6 cm, height 32 cm) with fractional elution using CH$_2$Cl$_2$ and CH$_2$Cl$_2$/EtOH mixtures. Fractions which were unary according to TLC were combined and produced 5.7 g of virtually pure cis-2-(2,4-dichlorophenyl)-2-(imidazol-1-ylmethyl)-4-[4-(4-benzoxazol-2-ylmethyl)piperazin-1-yl)phenoxymethyl]-1,3-dioxolane, which was recrystallized from methanol. 3.75 g (50.3% of theory) of virtually pure compound, melting point 139°-40° C., were obtained, analysis: $C_{32}H_{31}Cl_2N_5O_4$ (MW 620.55) calc. C 61.94, H 5.04, N 11.29; found C 61.7, H 5.1, N 11.2%.

EXAMPLE 15

In prinipally the same fashion as described in Example 14, 1.19 g (10.6 mmol) of potassium tert.-butylate were added to 10 mmol of 4-(4-hydroxyphenyl)-1-(benzoxazol-2-ylmethyl)-piperazine in 90 ml of absolute 1,2-dimethoxyethane, 10 mmol of IIb were subsequently added after stirring for 10 minutes, and the mixture was refluxed for 6 hours. After evaporation of the solvent in vacuo, the mixture was worked up and chromatographed as described in Example 14. 2.78 g (44.8% of theory) of cis-2-(2,4-dichlorophenyl)-2-(imidazol-1-ylmethyl)-4-[4-(4-benzoxazol-2-ylmethyl)-piperazin-1-yl)phenoxymethyl]-1,3-dioxolane, melting point 139°-40° C., were obtained after recrystallization from methanol.

EXAMPLE 16

The compounds of the formula Ib shown in Table 4 were prepared by process version (A) by the same procedure as described in Example 14, starting from IIb or IIc and in each case the appropriate 4-(4-hydroxyphenyl)piperazin-1-yl derivative of the formula IIId (M=H, Z=O, L=1).

TABLE 4

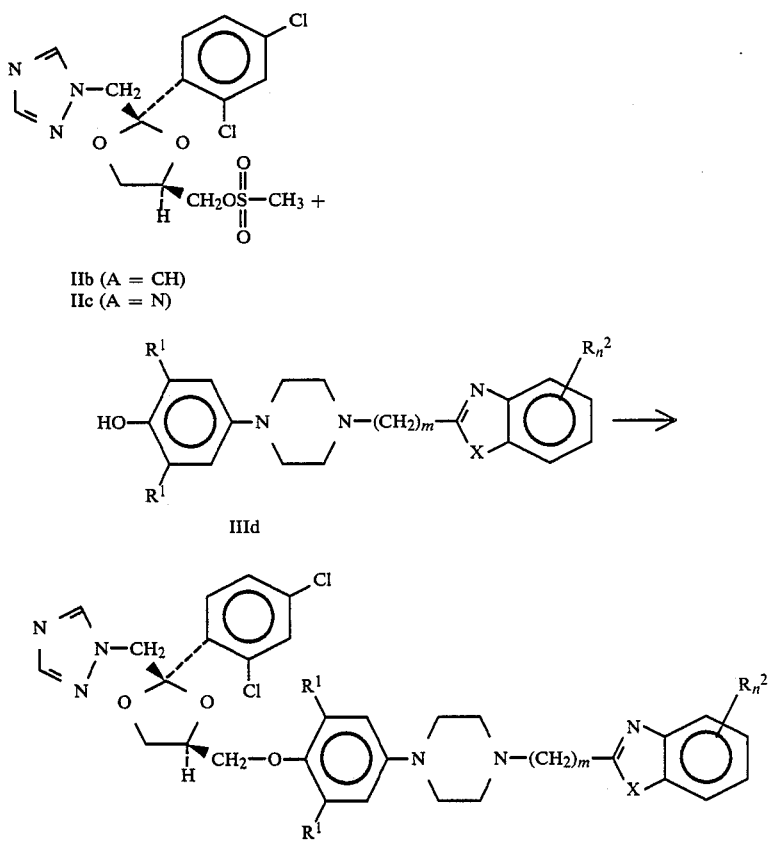

IIb (A = CH)
IIc (A = N)

IIId

Ib (p = O, Z = O)

| Comp. No. | A | R$^1$ | m | X | R$^2$ | n | | Analysis % Calc. | Found | m.p. [°C.] |
|---|---|---|---|---|---|---|---|---|---|---|
| 4.1 | N | H | 1 | O | — | 0 | C | 59.91 | 60.0 | 148–9 |
|  |  |  |  |  |  |  | H | 4.87 | 5.0 |  |
|  |  |  |  |  |  |  | N | 13.52 | 13.4 |  |
| 4.2 | CH | H | 1 | O | 5.6-(CH$_3$)$_2$ | 2 | C | 62.96 | 63.1 | 156–7 |
|  |  |  |  |  |  |  | H | 5.44 | 5.6 |  |
|  |  |  |  |  |  |  | N | 10.80 | 10.4 |  |

TABLE 4-continued
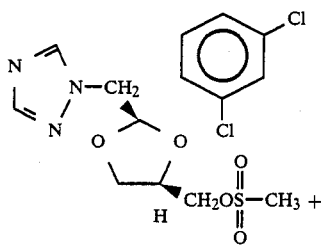
IIb (A = CH)
IIc (A = N)
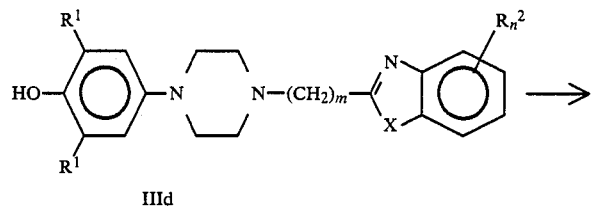
IIId
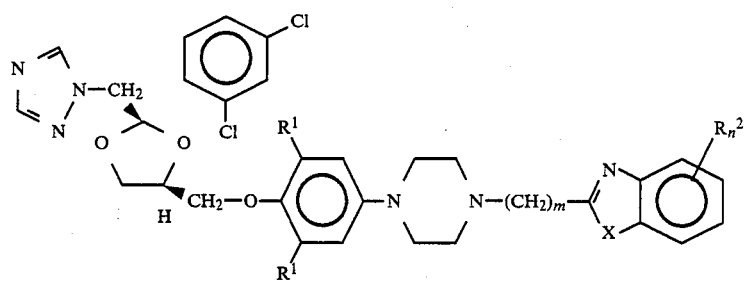
Ib (p = O, Z = O)
| Comp. No. | A | R¹ | m | X | R² | n | | Analysis % Calc. | Found | m.p. [°C.] |
|---|---|---|---|---|---|---|---|---|---|---|
| 4.3 | N | H | 1 | O | 5.6-(CH$_3$)$_2$ | 2 | C | 61.02 | 60.7 | 165–6 |
| | | | | | | | H | 5.28 | 5.3 | |
| | | | | | | | N | 12.94 | 12.7 | |
| 4.4 | CH | H | 1 | O | 5-Cl | 1 | C | 58.68 | 58.7 | — |
| | | | | | | | H | 4.62 | 4.9 | |
| | | | | | | | N | 10.69 | 10.6 | |
| 4.5 | N | H | 1 | O | 5-Cl | 1 | C | 56.76 | 56.6 | — |
| | | | | | | | H | 4.46 | 4.4 | |
| | | | | | | | N | 12.80 | 12.4 | |
| 4.6 | CH | H | 1 | S | — | 0 | C | 60.37 | 59.6 | 135–6 |
| | | | | | | | H | 4.91 | 4.9 | |
| | | | | | | | N | 11.00 | 10.7 | |
| 4.7 | N | H | 1 | S | — | 0 | C | 58.40 | 58.1 | 125–6 |
| | | | | | | | | 4.74 | 4.7 | |
| | | | | | | | N | 13.18 | 13.4 | |
| 4.8 | CH | H | 1 | O | 4,5-C₄H₄ | 2 | C | 64.48 | 64.2 | 183–4 |
| | | | | | | | H | 4.96 | 4.9 | |
| | | | | | | | N | 10.45 | 10.0 | |
| 4.9 | CH | CH$_3$ | 1 | O | — | 0 | C | 62.96 | 62.7 | — |
| | | | | | | | H | 5.44 | 5.3 | |
| | | | | | | | N | 10.80 | 10.8 | |
| 4.10 | CH | CH$_3$ | 1 | S | — | 0 | C | 61.44 | 61.1 | — |
| | | | | | | | H | 5.31 | 5.0 | |
| | | | | | | | N | 10.54 | 10.3 | |
| 4.11 | CH | H | 3 | O | — | 0 | C | 62.96 | 62.4 | — |
| | | | | | | | H | 5.44 | 5.5 | |
| | | | | | | | N | 10.80 | 10.5 | |
| 4.12 | N | H | 3 | O | — | 0 | C | 61.02 | 60.8 | 83–4 |

TABLE 4-continued

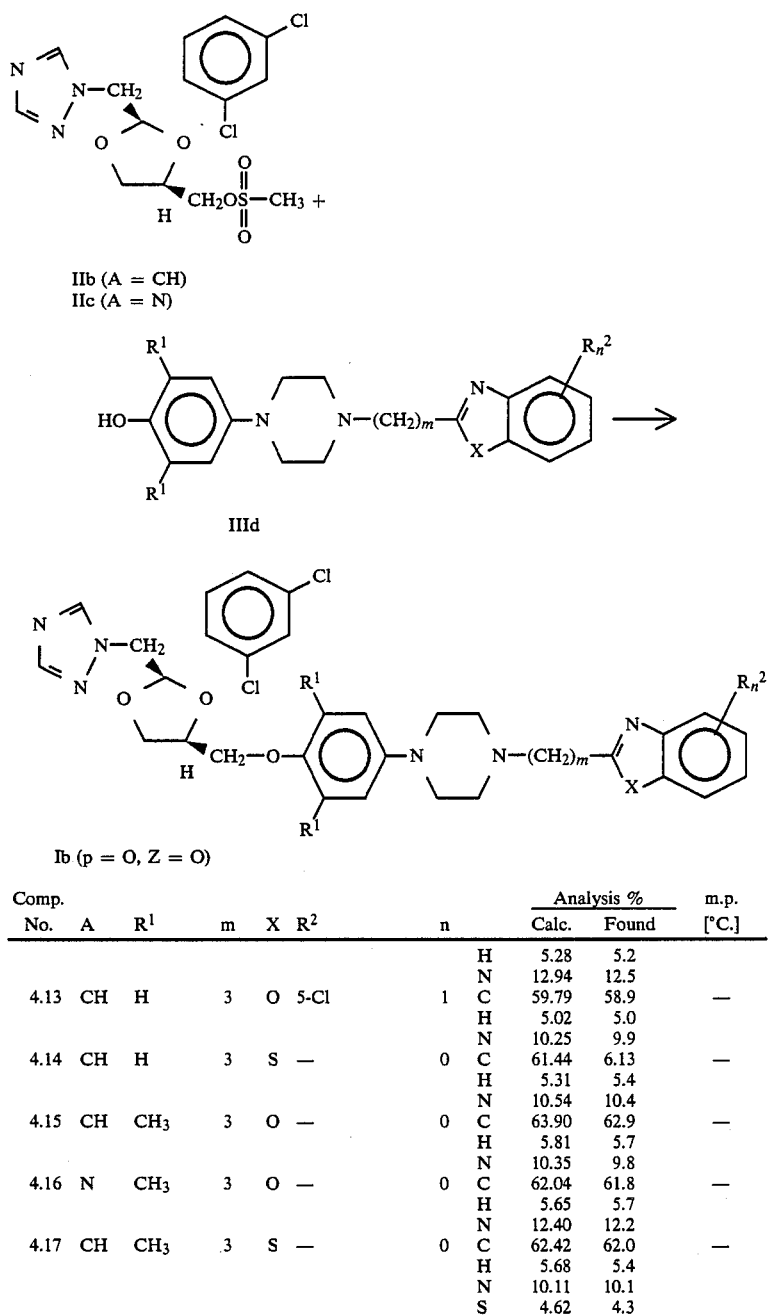

IIb (A = CH)
IIc (A = N)

IIId

Ib (p = O, Z = O)

| Comp. No. | A | R¹ | m | X | R² | n | | Analysis % Calc. | Found | m.p. [°C.] |
|---|---|---|---|---|---|---|---|---|---|---|
| | | | | | | | H | 5.28 | 5.2 | |
| | | | | | | | N | 12.94 | 12.5 | |
| 4.13 | CH | H | 3 | O | 5-Cl | 1 | C | 59.79 | 58.9 | — |
| | | | | | | | H | 5.02 | 5.0 | |
| | | | | | | | N | 10.25 | 9.9 | |
| 4.14 | CH | H | 3 | S | — | 0 | C | 61.44 | 6.13 | — |
| | | | | | | | H | 5.31 | 5.4 | |
| | | | | | | | N | 10.54 | 10.4 | |
| 4.15 | CH | CH₃ | 3 | O | — | 0 | C | 63.90 | 62.9 | — |
| | | | | | | | H | 5.81 | 5.7 | |
| | | | | | | | N | 10.35 | 9.8 | |
| 4.16 | N | CH₃ | 3 | O | — | 0 | C | 62.04 | 61.8 | — |
| | | | | | | | H | 5.65 | 5.7 | |
| | | | | | | | N | 12.40 | 12.2 | |
| 4.17 | CH | CH₃ | 3 | S | — | 0 | C | 62.42 | 62.0 | — |
| | | | | | | | H | 5.68 | 5.4 | |
| | | | | | | | N | 10.11 | 10.1 | |
| | | | | | | | S | 4.62 | 4.3 | |

EXAMPLE 17

154 mg (5.13 mmol) of an 80% strength NaH/oil dispersion were added to a solution of 1.93 g (5 mmol) of 1-(4-hydroxyphenyl)-4-(4-benzoxazol-2-yl)benzyl)-piperazine in 20 ml of absolute DMF, and, when the $H_2$ evolution was complete, a solution of 2.09 g (5.14 mmol) of cis-2-(2,4-dichlorophenyl)-2-imidazol-1-ylmethyl)-4-methanesulfonyloxymethyl-1,3-dioxolane (IIb) in 15 ml of absolute DMF was added, and the mixture was stirred for 8 hours at 100° C. The subsequent workup was carried out according to the procedure described in Example 12. The residue from the methylene chloride extract (3.5 g) was chromatographed as described in Example 14 on a silica gel S/CH₂Cl₂ column (diameter 2.0 cm, height 30 cm). After purification and evaporation of the unary fractions, 1.79 g (51% of theory) of cis-(2,4-dichlorophenyl)-2-(imidazol-1-ylmethyl)-4-[4-(4-(4-benzoxazol-2-yl)benzyl)piperazin-1-yl)phenoxymethyl]-1,3-dioxolane were obtained as a highly viscous oil, analysis: (MW 696.65) calc. C 65.52, H 5.06, N, 10.05; found C 65.6, H 5.1, N 9.7%.

Using the same procedure, starting from the methane sulfonate IIc, the corresponding 1,2,4-triazol-1-ylmethyl compound, cis-2-(2,4-dichlorophenyl)-2-(1,2,4-triazol-1-ylmethyl)-4-[4-(4-(4-(benzoxazol-2-yl)benzyl)piperazin-1-yl)phenoxmethyl]-1,3-dioxolane was obtained as a highly active oil. This substance was converted in methanol into the monohydrochloride, melting point 140°-1° C., using HCl/ether.

analysis: $C_{37}H_{35}Cl_3N_6O_4$ (MW 734.11), calc. C 60.54, H 4.81, N 11.45, Cl− 4.83; found C 60.0, H 4.8, N 10.9, Cl⊖ 5.3%;

Yield: 32% of theory.

EXAMPLE 18

The following were prepared according to the procedure as described in Example 17: Cis-2-(2,4-dichlorophenyl)-2-(imidazol-1-ylmethyl)-4-[4-(4-(4-(benzothiazol-2-yl)benzyl)piperazin-1-yl)phenoxymethyl]-1,3-dioxolane, melting point 156°-7° C., analysis: $C_{38}H_{35}Cl_2N_5O_3S$ (MW 712.72) calc. C 64.04, H 4.95, N 9.83; found C 64.3, H 5.0, N 9.8%, Cis-2-(2,4-dichlorophenyl)-2-(1,2,4-triazol-1-ylmethyl)-4-[4-(4-(4-(benzothiazol-2-yl)benzylpiperazin-1-yl)phenoxymethyl]-1,3-dioxolane, melting point 164°-5° C., analysis: $C_{37}H_{34}Cl_2N_6O_3S$ (MW 713.71) calc. C 62.27, H 4.80, N 11.78 found C 62.5, H 4.8, N 11.7%.

EXAMPLE 19

A solution of 3.25 g (10 mmol) of 4-(4-hydroxyphenyl)-1-(benzothiazol-2-ylmethyl)piperazine in 30 ml of absolute ethanol was added dropwise with stirring to a freshly prepared solution of 230 mg of sodium in 20 ml of absolute ethanol at room temperature, the mixture was stirred for a further 15 minutes, 4.07 g of IIb were added in portions at room temperature, and the mixture was subsequently refluxed for 6 hours. The ethanol was then removed by distillation in vacuo in a rotary evaporator, and the residue was taken up in 80 ml of $CH_2Cl_2$ and 25 ml of water. After mixing thoroughly and separating the phases, the aqueous phase was extracted a further twice with $CH_2Cl_2$. The combined $CH_2Cl_2$ extracts were dried, filtered and evaporated in vacuo. The residue from the extract (6.7 g) was dissolved in 15 ml of ethyl acetate, and ether was added until just before the turbidity limit.

Crystallization occurred after trituration. The product filtered off under suction was again recrystallized from ethyl acetate. 3.92 g of pure cis-2-(2,4-dichlorophenyl)-2-(imidazol-1-ylmethyl)-4-[4-(4-(benzothiazol-2-ylmethyl)piperazin-1-yl)phenoxymethyl]-1,3-dioxolane, melting point 135°-36° C. were obtained (cf. Example 16, Table 4, No. 4.6).

EXAMPLE 20

A mixture of 2.56 g (7.6 mmol) of 4-(4-hydroxy-3,5-dimethylphenyl)-1-(benzoxazol-2-ylmethyl)piperazine, 40 ml of toluene, 8 ml of 50% strength sodium hydroxide solution, 2.86 g (7 mmol) of IIb (cf. Table 2) and 0.35 g of tetrabutylammonium bromide was stirred vigorously for 3.5 hours at 100° C. The phases were then separated, and the concentrated sodium hydroxide solution was washed out twice with ether. The combined organic phases were washed twice with water, dried, filtered and evaporated in vacuo. The residue from the extract (4.3 g) was chromatographed as described in Example 14 on a silica gel S/$CH_2Cl_2$ column (diameter 2.0 cm, height 30 cm). 3.15 g (69.4% of theory) of pure cis-2-(2,4-dichlorophenyl)-2-(imidazol-1-ylmethyl)-4-[4-(4-benzoxazol-2-ylmethyl)piperazin-1-yl)-2,6-dimethylphenoxymethyl]-1,3-dioxolane were obtained after combination and evaporation of the fractions which were unary according to TLC (cf. also Example 16, Table 4, No. 4.8), analysis: found C 62.6, H 5.3, N 10.5%.

By the same procedure, using IIb and the appropriate benzothiazol-2-ylmethylpiperazine compound, cis-2-(2,4-dichlorophenyl)-2-(imidazol-1-ylmethyl)-4-[4-(4-(benzothiazol-2-ylmethyl)piperazin-1-yl)-2,6-dimethylphenoxymethyl]-1,3-dioxolane was obtained in 79.3% yield (cf. also Example 16, Table 4, No. 4.9); analysis: found C 61.2, H 5.1, N 10.2%, and using IIb or IIc and 4-(4-hydroxy-3,5-dimethylphenyl)-1-(5-methylbenzoxazol-2-yl)piperazine, cis-2-(2,4-dichlorophenyl)-2-(imidazol-1-ylmethyl)-4-[4-(4-(5-methylbenzoxazol-2-yl)piperazin-1-yl)-2,6-dimethylphenoxymethyl]-1,3-dioxolane, yield 81.2%, melting point 160° C., analysis, calc. C 62.96, H 5.4, N 10.80; found C 62.5, H 5.3, N 10.6%; and the corresponding triazole compound cis-2-(2,4-dichlorophenyl)-2-(1,2,4-triazol-1-ylmethyl)-4-[4-(4-(5-methylbenzoxazol-2-yl)piperazin-1-yl)-2,6-dimethylphenoxymethyl]-1,3-dioxolane, yield 78.4%, highly viscous oil, analysis: calc. C 61.01, H 5.28, N 12.94; found C 61.1, H 5.1, N 12.7%, were obtained.

Furthermore, by the same procedure, starting from the 2-(4-chlorophenyl) compound analogous to IIb, and the appropriate piperazine derivative, cis-2-(4-chlorophenyl)-2-(imidazol-1-ylmethyl)-4-[4-(4-(5-ethylbenoxazol-2-yl)piperazin-1-yl)phenoxymethyl]-1,3-dioxolane, melting point 106°-8° C., was obtained in 70.2% yield, analysis: $C_{33}H_{34}ClN_5O_4$ (MW 600.13) calc. C 66.05, H 5.71, N 11.67; found C 65.7, H 5.6, N 11.3%.

EXAMPLES OF THE PREPARATION PROCESS VERSION (B)

EXAMPLE 21

(a) 0.60 g of an 80% strength sodium hydride/oil dispersion was added (with cooling) to a solution of 6.19 g (20 mmol) of 1-(4-hydroxyphenyl)-4-(benzoxazol-2-ylmethyl)piperazine in 70 ml of absolute N,N-dimethylformamide (DMF) at room temperature. When the evolution of hydrogen was complete, a solution of 8.40 g (20 mmol) of cis-2-bromomethyl-2-(2,4-dichlorophenyl)-4-methanesulfonyloxymethyl-1,3-dioxolane (cis and trans relate to the bromomethyl and methanesulfonyloxymethyl group in the 2 or 4 position of the dioxolane ring) in 25 ml of absolute DMF was added dropwise at room temperature, and the mixture was stirred for 8 hours at 60° C. The subsequent work-up and chromatography was carried out in the same fashion as described in Example 14. The chromatographic purification was carried out on a silica gel S/methylene chloride/petroleum ether 2:1 column (diameter 3.6 cm, height 44 cm). 8.6 g (68% of theory) of cis-2-bromomethyl-2-(2,4-dichlorophenyl)-4-[4-(4-(benzoxazol-2-ylmethyl)piperazin-1-yl)phenoxymethyl]-1,3-dioxolane were obtained as a viscous oil:

| analysis: $C_{29}H_{28}BrCl_2N_3O_4$ (MW 633.40) | calc. | C 54.99 H 4.46 Br 12.62 Cl 11.20 N 6.63 | found | C 54.1 H 4.2 Br 12.5 Cl 11.3 N 6.3 |
|---|---|---|---|---|

(b) 0.345 g (11.5 mmol) of an 80% strength NaH/oil dispersion was added to a solution of 0.782 g (11.2 mmol) of imidazole in 25 ml of absolute N,N-dimethylacetamide. When the evolution of hydrogen was complete, a solution of 6.33 g (10 mmol) of the bromomethyl compound prepared under (a) in 10 ml of absolute N,N-dimethylacetamide was added dropwise, and the mixture was subsequently refluxed for 24 hours. The mixture was then worked up and chromatographed as described in Example 14. The dimethylacetamide was removed by distillation in an oil-pump vacuum in a rotary evaporator. After chromatography 2.42 g of still slightly impure cis-2-(2,4-dichlorophenyl)-2-(imidazol-1-ylmethyl)-4-[4-(4-(benzoxazol-2-ylmethyl)piperazin-1-yl)phenoxymethyl]-1,3-dioxolane were obtained, which produced 2.07 g (33.4% of theory) of pure product (cf. Example 14), melting point 139°–40° C., recrystallized from methanol.

EXAMPLE 22

(a) By the same procedure as described in Example 21a, starting from 1-(4-hydroxyphenyl)-4-(6-chlorobenzothiazol-2-yl)piperazine and cis-2-bromomethyl-2-(2,4-dichlorophenyl)-4-methanesulfonyloxymethyl-1,3-dioxolane, cis-2-bromomethyl-2-(2,4-dichlorophenyl)-4-[4-(4-(6-chlorobenzothiazol-2-yl)piperazin-1-yl)phenoxymethyl]-1,3-dioxolane, melting point 129°–130° C., was prepared in 65% yield:

| analysis: | calc. | | found | |
|---|---|---|---|---|
| $C_{28}H_{25}BrCl_3N_3O_3S$ | | C 50.20 | | C 50.3 |
| (MW 669.89) | | H 3.76 | | H 3.7 |
| | | Br 11.93 | | Br 12.1 |
| | | Cl 15.88 | | Cl 16.0 |
| | | N 6.27 | | N 6.1 |
| | | S 4.79 | | S 5.2 |

(b) By the same procedure as described in Example 21b starting from 0.794 g (11.5 mmol) of 1,2,4-triazole, 0.345 g (11.5 mmol) of an 80% strength NaH/oil dispersion and 6.7 g (10 mmol) of the cis-2-bromomethyl-2-(2,4-dichlorophenyl)-4-[4-(4-(6-chlorobenzothiazol-2-yl)piperazin-1-yl)phenoxymethyl]-1,3-dioxolane prepared under a), cis-2-(2,4-dichlorophenyl)-2-(1,2,4-triazol-1-ylmethyl)-4-[4-(4-(6-chlorobenzothiazol-2-yl)piperazin-1-yl)phenoxymethyl]-1,3-dioxolane (2.05 g≙31.2% yield), melting point 146°–47° C., was prepared in absolute N,N-dimethylacetamide. The substance had been recrystallized from methanol after chromatographic purification. A solution of 1.023 g (14.83 mmol) of 1,2,4-triazole in 4 ml of absolute dimethyl sulfoxide (DMSO) was added dropwise to a suspension of 0.49 g (16.3 mmol) of an 80% strength NaH/oil dispersion in 15 ml of absolute DMSO at room temperature, the mixture was stirred for a further 30 minutes at room temperature, and 6.7 g (10 mmol) of cis-2-bromomethyl-2-(2,4-dichlorophenyl)-4-[4-(4-(6-chlorobenzothiazol-2-yl)piperazin-1-yl)phenoxymethyl]-1,3-dioxolane, prepared according to Example 22a and dissolved in 6 ml of absolute DMSO, was subsequently added dropwise, and the mixture was stirred for 16 hours at 130° C. under a nitrogen atmosphere. After cooling, the reaction mixture was stirred into 100 ml of water. This mixture was extracted repeatedly with $CH_2Cl_2$. The combined $CH_2Cl_2$ extracts were dried, filtered and evaporated in vacuo. The residue (6.7 g) was purified as described in Example 14 by column chromatography on silica gel S. The combined fractions which were unary according to TLC produced, after evaporation, a crystalline residue which was mixed with hexane and filtered off under suction. 2.62 g (39.8% of theory) of pure compound, melting point 146°–7° C., were obtained (cf. also Example 13, Table 3, No. 3.5).

EXAMPLE 24

A mixture of 2.42 g (7 mmol) of 1-(4-hydroxyphenyl)-4-(6-chlorobenzothiazol-2-yl)piperazine, 100 ml of toluene, 2.94 g (7 mmol) of 2-bromomethyl-2-(2,4-dichlorophenyl)-4-methanesulfonyloxymethyl-1,3-dioxolane, 0.50 g of tetrabutylammonium bromide and 14 ml of 50% strength sodium hydroxide solution was stirred vigorously for 12 hours at 65° C. The cooled mixture was subsequently filtered under suction in order to separate off the hydroxyphenyl-(6-chlorobenzothiazol-2-yl)piperazine remaining as a solid. 0.58 g (≙24% of the amount used) of this starting material were recovered unchanged in this fashion. The phases of the clear filtrate were separated. The toluene solution was shaken twice with water, dried, filtered and evaporated in vacuo. The residue remaining was dissolved in boiling acetonitrile. On cooling the solution, a crystalline precipitate was produced. This was recrystallized a further twice from acetonitrile (filtered whilst hot in between). 2.49 g (70% of theory relative to the reacted phenol derivative) of pure 2-bromomethyl-2-(2,4-dichlorophenyl)-4-[4-(4-(6-chlorobenzothiazol-2-yl)piperazin-1-yl)phenoxymethyl]-1,3-dioxolane (mixture of cis/trans diasteromers), melting point 115°–16° C., were obtained, analysis: found C 50.2, H 3.7, Br 12.2, Cl 15.9, N 6.3, S 5.3 (calc. cf. Example 22a).

EXAMPLES OF THE PREPARATION PROCESS VERSION (C)

EXAMPLE 25

A mixture of 300 ml of benzene and 10.5 g (55 mmol) of p-toluenesulfonic acid monohydrate was first boiled on a water separator until anhydrous. 17.1 g (40 mmol) of α-(imidazol-1-yl)-2,4-dichloroacetophenone p-toluenesulfate, 150 ml of n-butanol and 11.58 g (48 mmol) of 1-(benzothiazol-2-ylthio)-2,3-dihydroxypropane were subsequently added to the cooled solution, and the solution was refluxed for 48 hours on a water separator. The cooled solution was then shaken three times with 65 ml of NaOH in each case and subsequently twice with water, and the benzene solution was dried using $Na_2SO_4$, filtered and evaporated in vacuo. The residue was dissolved in 35 ml of methanol, whereupon a solid crystallized out. This was filtered off under suction and proved to be pure α-(imidazol-1-yl)-2,4-dichloroacetophenone. 6.32 g (62% of the amount used) of this starting ketone were obtained. The methanol mother liquor was evaporated in vacuo. The residue was chromatographed as described in Example 14 on a silica gel S/$CH_2Cl_2$ column (diameter 2.1 cm, height 40 cm). The fractions which were unary according to TLC (TLC comparison with the product prepared according to Example 3) were combined and evaporated in vacuo. 0.84 g (4.4% of theory) of cis/trans-2-(2,4-dichlorophenyl)-2-(imidazol-1-ylmethyl)-4-benzothiazol-2-ylthiomethyl)-1,3-dioxolane, pure according to TLC, was obtained as a highly viscous oil, analysis: found C 51.6, H 3.4 N 8.2%.

EXAMPLES OF THE PREPARATION PROCESS VERSION (D)

EXAMPLE 26

A solution of 2.45 g (5 mmol) of 2-S,(R)-(2,4-dichlorophenyl)-2-(imidazol-1-ylmethyl)-4-R,(S)-(4-piperazinophenoxymethyl)-1,3-dioxolane (cis form) and 1.01 g (5 mmol) of 5-chloro-2-chloromethylbenzoxazole in 20 ml of absolute DMF was warmed to 80° C. under protection against atmospheric humidity, and 115 mg of finely powdered potassium carbonate were added after 10 minutes with stirring. A further 115 mg of powdered $K_2CO_3$ were added after a further 25 minutes, and a 3rd portion of 115 mg of powdered $K_2CO_3$ were added after a further 60 minutes (a total of 345 mg (2.5 mmol) of $K_2CO_3$). The mixture was subsequently stirred for a further 3 hours at 80° C., the DMF was removed by distillation in an oil-pump vacuum in a rotary evaporator, and the residue was taken up in 30 ml of water and 100 ml of $CH_2Cl_2$. After separating the phases, the aqueous phase was extracted a further twice with $CH_2Cl_2$. The combined $CH_2Cl_2$ extracts were dried, filtered and evaporated in vacuo. The residue (3.6 g) was purified as described in Example 14 by column chromatography on silica gel $S/CH_2Cl_2$. 2.75 g (84% of theory) of pure cis-2-(2,4-dichlorophenyl)-2-(imidazol-1-ylmethyl)-4[4-(4-(5-chlorobenzoxazol-2-ylmethyl)-piperazin-1-yl)phenoxy-methyl]-1,3-dioxolane were obtained as a highly viscous oil;

analysis: found: C 58.6, H 4.7, N 10.6%. (cf. Example 16, Table 4, No. 4.4).

EXAMPLE 27

The compounds of the formula I shown in Table 5 were prepared by process version (D) by the same procedure as described in Example 26, starting from IXa or IXb (cf. Table 5) and in each case the appropriate chlorine compound of the formula Xa or XIa.

TABLE 5

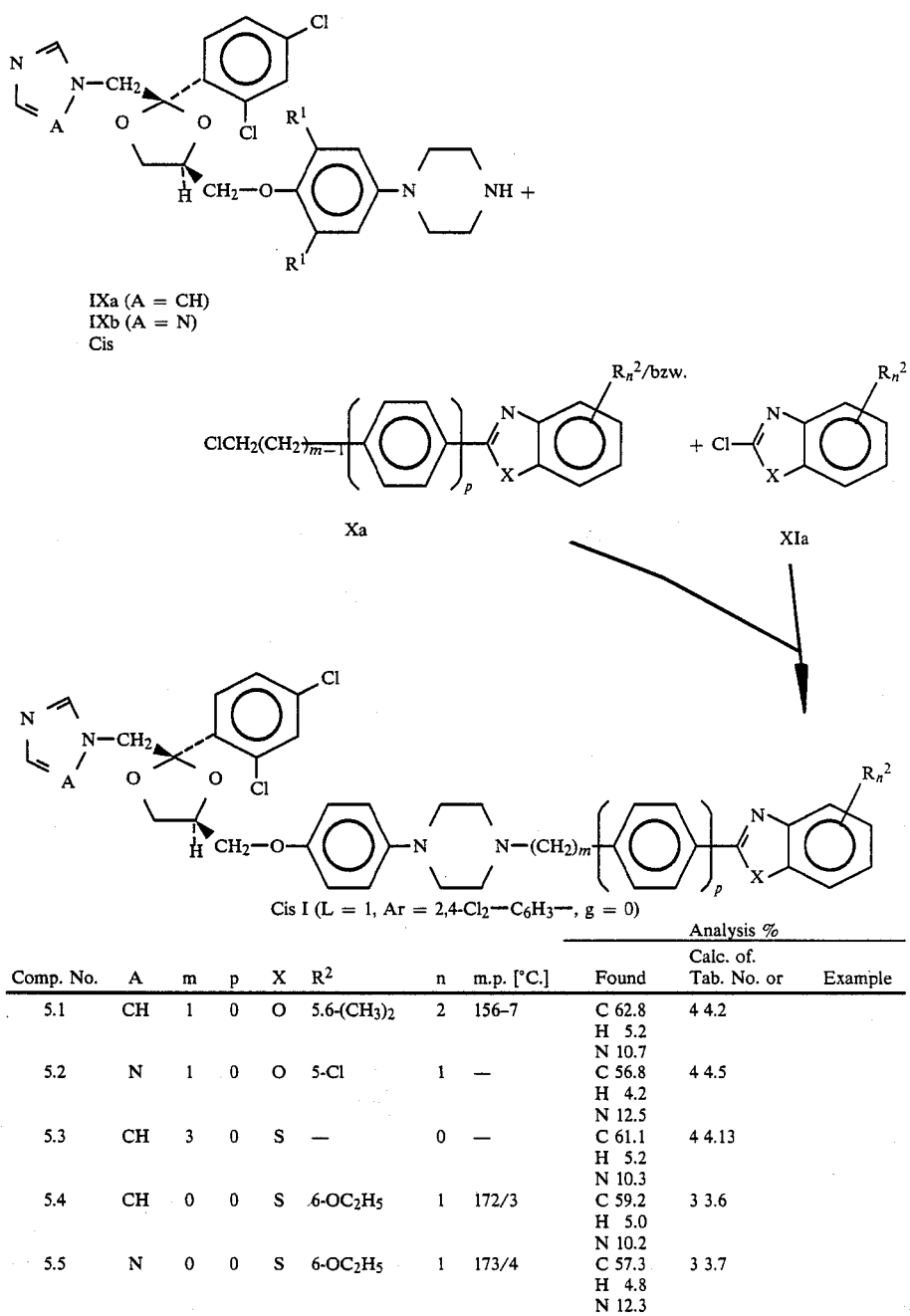

| Comp. No. | A | m | p | X | $R^2$ | n | m.p. [°C.] | Found | Calc. of. Tab. No. or | Example |
|---|---|---|---|---|---|---|---|---|---|---|
| 5.1 | CH | 1 | 0 | O | 5.6-$(CH_3)_2$ | 2 | 156–7 | C 62.8 H 5.2 N 10.7 | 4 4.2 | |
| 5.2 | N | 1 | 0 | O | 5-Cl | 1 | — | C 56.8 H 4.2 N 12.5 | 4 4.5 | |
| 5.3 | CH | 3 | 0 | S | — | 0 | — | C 61.1 H 5.2 N 10.3 | 4 4.13 | |
| 5.4 | CH | 0 | 0 | S | 6-$OC_2H_5$ | 1 | 172/3 | C 59.2 H 5.0 N 10.2 | 3 3.6 | |
| 5.5 | N | 0 | 0 | S | 6-$OC_2H_5$ | 1 | 173/4 | C 57.3 H 4.8 N 12.3 | 3 3.7 | |

TABLE 5-continued

| 5.6 | CH | 1 | 1 | O | — | 0 | — | C 65.4<br>H 5.1<br>N 9.9 | 17 |
|---|---|---|---|---|---|---|---|---|---|
| 5.7 | N | 1 | 1 | S | — | 0 | 164/5 | C 62.0<br>H 4.6<br>N 11.6 | 18 |

EXAMPLE 28

By principally the same procedure as described in Example 26 starting from 5 mmol of IXa and 5 mmol of 5-chloro-2-chloromethylbenzoxazole, but in 50 ml of absolute acetonitrile as solvent in place in DMF, 2.20 g (67.2% of theory) of cis-2-(2,4-dichlorophenyl)-2-(imidazol-1-ylmethyl)-4-[4-(4-(5-chlorobenzoxazol-2-ylmethyl)piperazin-1-yl)phenoxymethyl]-1,3-dioxolane (oil) were obtained after purification by chromatography.

EXAMPLES OF THE PREPARATION OF COMPOUNDS OF THE FORMULA IIIa

EXAMPLE 29

A mixture of 5.11 g (15 mmol) of 1-(4-hydroxyphenyl)piperazine dihydrobromide, 2.46 g (16 mmol) of 2-chlorobenzoxazole and 2.18 g (15.8 mmol) of powdered $K_2CO_3$ in 55 ml of absolute N,N-dimethylformamide was warmed to 85° C., and 345 mg of powdered $K_2CO_3$ were added with stirring under a nitrogen atmosphere in each case after 10 minutes, after a further 25 minutes and after a further 60 minutes (total addition of 1.035 g (7.5 mmol) of $K_2CO_3$). The mixture was stirred for a further 3 hours at 85° C., the DMF was substantially removed by distillation in an oil-pump vacuum in a rotary evaporator, the crystalline residue was mixed with 50 ml of water, and this mixture was shaken for 15 minutes. The mixture was then filtered under suction and the filter residue was washed with water and dried in vacuo. 4.30 g (97% of theory) of pure 1-(4-hydroxyphenyl)-4-(benzoxazol-2-yl)piperazine, melting point 161°-3° C., were obtained,

| analysis: | calc. | C 69.13 | found | C 69.1% |
|---|---|---|---|---|
| $C_{17}H_{17}N_3O_2$ | | H 5.80 | | H 5.7 |
| (MW 295.35) | | N 14.23 | | N 14.1 |

EXAMPLE 30

The compounds of the formula IIIa shown in Table 6 were prepared by the same procedure as described in Example 29, starting from a compound of the formula XVI and in each case the appropriate 2-chlorobenzazole of the formula XIa.

TABLE 6

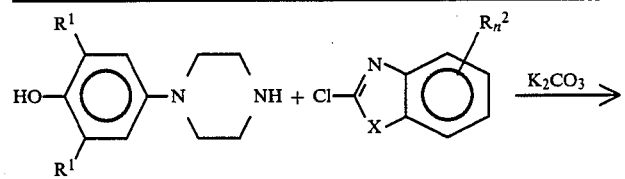

XVI      XIa

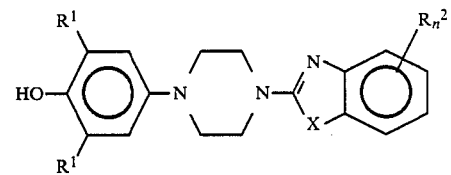

IIIa (m and p = O)

| Comp. No. | $R^1$ | X | $R^2$ | n | Yield [%] | m.p. [°C.] | Empirical formula (MW) | Analysis % Calc. | Found |
|---|---|---|---|---|---|---|---|---|---|
| 6.1 | H | O | 6-Cl | 1 | 93 | 195-6 | $C_{17}H_{16}ClN_3O_2$<br>(329.80) | C 61.91<br>H 4.89<br>N 12.74 | 61.8<br>4.8<br>12.6 |
| 6.2 | H | O | 5-$CH_3$ | 1 | 83 | 205-6 | $C_{18}H_{19}N_3O_2$<br>(309.37) | C 69.88<br>H 6.19<br>N 13.58 | 69.8<br>6.2<br>13.4 |
| 6.3 | $CH_3$ | O | 5-$CH_3$ | 1 | 92 | 202-3 | $C_{20}H_{23}N_3O_2$<br>(337.43) | C 71.19<br>H 6.87<br>N 12.45 | 71.0<br>6.8<br>12.2 |
| 6.4 | H | S | 6-Cl | 1 | 98 | 183-4 | $C_{17}H_{16}ClN_3OS$<br>(345.86) | C 59.04<br>H 4.66<br>N 12.15 | 59.0<br>4.7<br>12.0 |
| 6.5 | H | S | 6-$OC_2H_5$ | 1 | 61 | 189-90 | $C_{19}H_{21}N_3O_2S$<br>(355.47) | C 64.20<br>H 5.96<br>N 11.82 | 63.5<br>5.9<br>11.6 |
| 6.6 | $CH_3$ | S | 5-Cl<br>6-$CH_3$ | 2 | | 211-2 | $C_{20}H_{22}ClN_3OS$<br>(387.94) | C 61.92<br>H 5.72 | 61.7<br>5.7 |

TABLE 6-continued

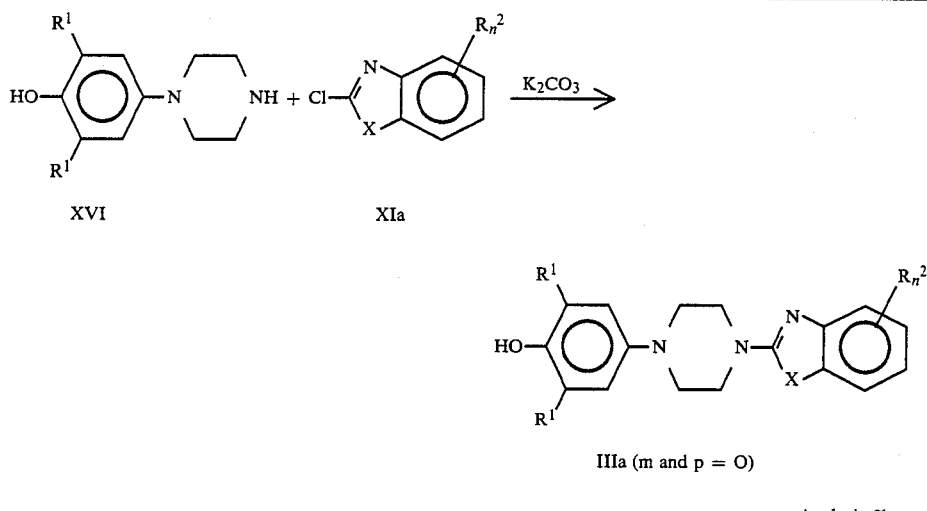

IIIa (m and p = O)

| Comp. No. | R¹ | X | R² | n | Yield [%] | m.p. [°C.] | Empirical formula (MW) | Analysis % Calc. | Found |
|---|---|---|---|---|---|---|---|---|---|
| | | | | | | | | N 10.83 | 10.5 |

EXAMPLE 31

A mixture of 6.06 g (34 mmol) of 1-(4-hydroxyphenyl)piperazine and 5.36 g (32 mmol) of 2-chloromethylbenzoxazole in 100 ml of absolute DMF was warmed to 80° C., and 737 mg of powdered $K_2CO_3$ were added with stirring (under a nitrogen atmosphere) in each case after 10 minutes, after a further 25 minutes and after a further 60 minutes (total addition of 2.21 g (16 mmol) of $K_2CO_3$). The mixture was stirred for a further 3 hours at 80° C., the DMF was substantially removed by distillation in vacuo, and the residue was taken up in 200 ml of ether and 100 ml of water. After separating the phases, the aqueous phase was extracted a further twice with ether. The combined ether extracts were dried, filtered and evaporated in vacuo. The residue was taken up in diisopropyl ether, whereafter crystallization occurred. The crystalline substance was filtered off under suction. 7.10 g (71.7% of theory) of 1-(4-hydroxyphenyl)-4-(benzoxazol-2-ylmethyl)piperazine, melting point 155°-56° C., were obtained, analysis: $C_{18}H_{19}N_3O_2$ (MW 309.37) calc. C 69.88, H 6.19, N 13.58; found C 69.9, H 6.0, N 13.3%.

EXAMPLE 32

The compounds of the formula IIIa shown in Table 7 were prepared by the same procedure as described in Example 31, starting from a compound of the formula XVI and in each case the appropriate compound of the formula Xa. If, after the evaporation of the DMF from the reaction mixture, a solid, crystalline residue remained, this was worked up further according to the procedure as described in Example 29. This was the case in the majority of the examples collated in Table 7. If a residue which was partially solid and partially a viscous oil remained at the said point, further work-up was then effected as described in Example 31.

Ether (as in Example 31) or methylene chloride was used as extractant. If compounds of the formula IIIa which were primarily isolated in crystalline form in the presence of water were produced in not entirely pure form according to TLC, the suspensions thereof were refluxed in ethyl acetate for 2-10 minutes, cooled, and the crystalline compound isolated by filtering off under suction. When using compounds Xa where m=3, 30 mol% of powdered sodium iodide were additionally added to the reaction mixture.

TABLE 7

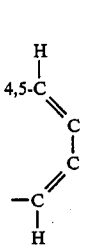

| Comp. No. | $R^1$ | m | p | X | $R^2$ | n | Yield [%] | m.p. [°C] | Empirical formula (MW) | Analysis % Calc. | Found |
|---|---|---|---|---|---|---|---|---|---|---|---|
| 7.1 | H | 1 | 0 | O | 5-Cl | 1 | 95 | 145-6 | $C_{18}H_{18}ClN_3O_2$ (343.82) | C 62.88<br>H 5.28<br>Cl 10.31<br>N 12.22 | 62.6<br>5.2<br>10.6<br>12.2 |
| 7.2 | H | 1 | 0 | O | 5,6-$(CH_3)_2$ | 2 | 92 | 191-2 | $C_{20}H_{23}N_3O_2$ (337.43) | C 71.19<br>H 6.87<br>N 12.45 | 69.4<br>6.8<br>12.1 |
| 7.3 | H | 1 | 0 | S | — | 0 | | 175-6 | $C_{18}H_{19}N_3OS$ (325.44) | C 66.43<br>H 5.88<br>N 12.91 | 66.0<br>6.1<br>12.8 |
| 7.4 | H | 1 | 0 | O | 4,5-C=CH—CH=CH—C= | 2 | 89 | 208-9 | $C_{22}H_{21}N_3O_2$ (359.43) | C 73.52<br>H 5.89<br>N 11.69 | 73.2<br>5.7<br>11.7 |
| 7.5 | $CH_3$ | 1 | 0 | O | — | 0 | 70 | 118-9 | $C_{20}H_{23}N_3O_2$ (337.43) | C 71.19<br>H 6.87<br>N 12.45 | 70.7<br>6.6<br>12.2 |
| 7.6 | $CH_3$ | 1 | 0 | S | — | 0 | 55 | 143-4 | $C_{20}H_{23}N_3OS$ (353.49) | C 67.96<br>H 6.56<br>N 11.89<br>S 9.07 | 67.7<br>6.7<br>11.8<br>9.0 |
| 7.7 | H | 3 | 0 | O | — | 0 | 83 | 175-6 | $C_{20}H_{23}N_3O_2$ (337.43) | C 71.19<br>H 6.87<br>N 12.45 | 71.3<br>7.0<br>12.4 |
| 7.8 | H | 3 | 0 | O | 5-Cl | 1 | 83 | 110-11 | $C_{20}H_{22}ClN_3O_2$ (371.88) | C 64.60<br>H 5.96<br>Cl 9.53<br>N 11.30 | 63.05<br>6.0<br>9.7<br>10.95 |
| 7.9 | H | 3 | 0 | S | — | 0 | 38 | 127-8 | $C_{20}H_{23}N_3OS$ (353.49) | C 67.96<br>H 6.56<br>N 11.89 | 68.4<br>6.6<br>12.2 |
| 7.10 | $CH_3$ | 3 | 0 | O | — | 0 | 77 | 121-2 | $C_{22}H_{27}N_3O_2$ (365.48) | C 72.30<br>H 7.45<br>N 11.50 | 72.0<br>7.6<br>11.4 |
| 7.11 | $CH_3$ | 3 | 0 | S | — | 0 | 35 | 140-2 | $C_{22}H_{27}N_3OS$ (381.55) | C 69.26<br>H 7.13<br>N 11.01 | 69.4<br>6.9<br>10.7 |
| 7.12 | H | 1 | 1 | O | — | 0 | 90 | 235-6 | $C_{24}H_{23}N_3O_2$ (385.47) | C 74.78<br>H 6.01<br>N 10.90 | 73.8<br>5.8<br>10.4 |
| 7.13 | H | 1 | 1 | S | — | 0 | 94 | 234-5 | $C_{24}H_{23}N_3OS$ (401.54) | C 71.80<br>H 5.77<br>N 10.47 | 71.7<br>5.9<br>14.3 |

EXAMPLE 33

A solution of 1.05 g of triethylamine in 20 ml of absolute dimethoxyethane was added dropwise within 15 minutes with stirring to a mixture of 1.78 g (10 mmol) of 1-(4-hydroxyphenyl)piperazine, 2.48 g (13.5 mmol) of 2-chloromethylbenzothiazole and 80 ml of absolute 1,2-dimethoxyethane under reflux. The mixture was stirred for a further 5 hours under reflux, the solvent was evaporated in vacuo, the residue was taken up in $CH_2Cl_2/H_2O$, the phases were separated, and the aqueous phase was extracted three times with $CH_2Cl_2$. The combined $CH_2Cl_2$ extracts were dried, filtered and evaporated. The crystalline residue (3.2 g) was recrystallized from methanol. 2.64 g (81.2% of theory) of pure 1-(4-hydroxyphenyl)-4-(benzothiazol-2-ylmethyl)piperazine, melting point 175°-76° C., were obtained.

It was also possible to carry out this synthesis using 1-(4-hydroxyphenyl)piperazine dihydrobromide. In this case, 3.10 g (30.7 mmol) of triethylamine were used in a 10 mmol batch, and the reaction time was extended to 18 hours. Approximately the same amount (2.6–2.7 g) of pure 1-(4-hydroxyphenyl)-4-(benzothiazol-2-ylmethyl)-piperazine were obtained using the base of the piperazine derivative as in the version above.

PREPARATION OF STARTING MATERIALS FOR THE PROCESS VERSION (C)

EXAMPLE 34

1.80 g (60 mmol) of an 80% strength NaH/oil dispersion were added (with cooling) to a solution of 10.04 g (60 mmol) of 2-mercaptobenzothiazole in 100 ml of absolute DMF at about 40° C., and the mixture was stirred for 15 minutes at 40° C., after which the evolution of hydrogen was complete. 6.63 g (5.02 ml, 60 mmol) of 1-chloro-2,3-dihydroxypropane and 0.30 g (2 mmol) of powdered sodium iodide were added, the mixture was stirred for 3 hours at 87° C., and the DMF was subsequently substantially removed by distillation in vacuo in a rotary evaporator. The oily residue was taken up in 300 ml of $CH_2Cl_2$, and the solution was successively shaken twice with 80 ml of 0.2N NaOH in each case and twice with water, dried, filtered and evaporated in vacuo. The residue remaining, 12.5 g of a viscous oil, was chromatographed on a silica gel S/$CH_2Cl_2$ column (diameter 2.0 cm, height 38 cm) by elution with $CH_2Cl_2$ and $CH_2Cl_2$/ethanol 100:0.5–100:3 (v/v) mixtures. The fractions which were unary according to TLC were combined and evaporated vigorously in an oil-pump vacuum. 9.0 g (62.2% of theory) of 1-(benzothiazol-2-ylthio)-2,3-dihydroxypropane, a compound of the formula VIII (Z=S, L, m and p=O) were obtained as a highly viscous oil, analysis: $C_{10}H_{11}NO_2S_2$ (MW 241.34) calc. C 49.77, H 4.59, N 5.80, S 26.57, found C 48.8, H 4.6, N 5.7, S 26.3%.

EXAMPLE 35

7.0 g (0.233 mol) of an 80% strength NaH/oil dispersion were added with cooling and stirring to a mixture of 108 g (1.17 mol) of anhydrous glycerol and 1,200 ml of absolute 1,2-dimethoxyethane, the mixture was stirred vigorously for 6 hours at 50° C., 36.72 g (0.18 mol) of 2,6-dichlorobenzothiazole were subsequently added, and the mixture was refluxed with vigorous stirring for 15 hours. The dimethoxyethane solution of the viscous oil phase (glycerole) was then decanted off at room temperature, and the glycerole phase was extracted successively by stirring under reflux three times with dimethoxyethane. The combined dimethoxyethane solutions were evaporated in vacuo. The oily residue was taken up in 1000 ml of $CH_2Cl_2$ and 600 ml of aqueous $NH_4Cl$ solution and mixed vigorously, and the phases were separated. The $CH_2Cl_2$ solution was washed with water, dried, filtered and evaporated in vacuo. The partly crystalline residue (28 g) was boiled for 10 minutes with 45 ml of chloroform, cooled and filtered off under suction. The filter residue (dried 8.9 g) was 6-chloro-2,3-dihydrobenzothiazol-2-one, which was formed as a byproduct. The filtrate residue (19.1 g) was chromatographed on a silica gel S/$CH_2Cl_2$ column (diameter 2.6 cm, height 35 cm). Elution was effected with $CH_2Cl_2$ and $CH_2Cl_2$/ethanol 100:0.5–100:5 (v/v) mixtures. Besides unreacted 2,6-dichlorobenzothiazole, a further amount of 6-chloro-2,3-dihydrobenzothiazol-2-one (in total 11 g) was eluted first. About 8 g of highly concentrated 1-(6-chlorobenzothiazol-2-yloxy)-2,3-dihydroxypropane, which was recrystallized from acetonitrile, were subsequently eluted. 6.30 g (13.5% of theory) of pure product, melting point 119°-20° C., were obtained,

| analysis: | calc. | C 46.25 | found | C 45.7% |
|---|---|---|---|---|
| $C_{10}H_{10}ClNO_3S$ | | H 3.88 | | H 3.6 |
| (MW 259.72) | | Cl 13.65 | | Cl 14.1 |
| | | N 5.39 | | N 5.4 |
| | | S 12.35 | | S 11.9 |

ANTIMYCOTIC ACTIVITY OF THE COMPOUNDS

The results of the treatment of laboratory animals which were infected experimentally with *trichophyton mentagrophytes* are given as an example of the high local in vivo activity of the compounds according to the invention. In order to determine the local activity, two guinea pigs (Pirbright white strain) weighing 450–500 g were each affected with $1.5 \times 10^4$ conidia/animal in the epidermis, distributed over 6 points of infection.

The animals were treated dermally on 5 successive days from the 3rd day after the infection by applying a 0.1% strength preparation solution to 3 points of infection on one back. The other back was treated in the same fashion with vehicle without preparation.

In addition to the animals treated with the substances according to the invention, two animals were treated with the reference substance terconazole, and two animals were not treated after the infection.

As can be seen from Table 8, the compounds according to the invention exhibited a markedly greater reduction of the mycosis diameter than did the standard preparation terconazole, i.e. the antimycotic effect of the compounds according to the invention was up to 80% superior to that of terconazole.

TABLE 8

| | | Mycoses (diameter in mm) | | | | | | |
|---|---|---|---|---|---|---|---|---|
| | Preparation | Vehicle controls | | | Preparation + Vehicle | | | Difference |
| Concentration | Example No. | $x_1$ | $(s)^{(2)}$ | $n^{(1)}$ | $x_2$ | $(s)$ | $n^{(1)}$ | $x_1-x_2$ (%) |
| dermal | | | | | | | | |
| 5 × 0.1% | (16) 4.2 | 14.3 | (2.8) | 6 | 4.1 | (1.1) | 6 | 10.2 (156.9) |
| | (16) 4.10 | 15.0 | (2.5) | 6 | 4.1 | (0.9) | 6 | 10.9 (167.6) |
| | (2) 1.4 base | 14.7 | (1.3) | 6 | 3.0 | (1.0) | 6 | 11.7 (180.0) |
| | terconazole | 13.8 | (1.7) | 6 | 7.3 | (1.8) | 6 | 6.5 (100.0) |

TABLE 8-continued

| Concentration | Preparation Example No. | Mycoses (diameter in mm) | | | | | | Difference |
|---|---|---|---|---|---|---|---|---|
| | | Vehicle controls | | | Preparation + Vehicle | | | |
| | | $x_1$ | $(s)^{(2)}$ | $n^{(1)}$ | $x_2$ | $(s)$ | $n^{(1)}$ | $x_1-x_2$ (%) |
| Controls, untreated infected animals | — | 14.6 | (3.9) | 12 | — | | | — |

$^{(1)}$n = Number of mesurements
$^{(2)}$(s) = Standard deviation

The results of the treatment of laboratory animals which were infected experimentally with Candida albicans are given as an example of the high oral and parenteral in vivo activity of the compounds according to the invention.

In order to determine the oral and parenteral activity, groups each comprising 5 mice weighing 18–20 g (strain HOE: NMRKF; SPF 71) were infected with $2.10^6$ germs/animal.

The animals were treated orally or subcutaneously in 8 identical individual doses each of 30 mg/kg or 10 mg/kg of body weight ($-24/-18/-2h/+2/24/30/48/54h$).

In addition to the groups of 5 animals treated with the substances I according to the invention, a group likewise of 5 animals was treated for comparison with the reference substance ketoconazole. A control group of 10 animals was not treated after the infection.

As can be seen from Table 9, the animals survived for up to twice as long after infection in the case of the compounds according to the invention, compared to the current standard preparation ketoconazole.

TABLE 9

| Dose | Preparation Example No. | No. of animals | Survival times days after infection | | | | | $\underline{x}$ Days | Survival time in % (standard prep. = 100%) |
|---|---|---|---|---|---|---|---|---|---|
| oral 8 × 30 mg/kg | (13) 3.3 | 5 | 11 | 11 | 14 | 14 | 14 | 12.8 | 177.7 |
| | (16) 4.2 | 5 | 8 | 9 | 9 | 10 | 14 | 10.0 | 138.8 |
| | (16) 4.4 | 5 | 6 | 6 | 10 | 14 | 14 | 10.0 | 138.8 |
| | ketoconazole | 5 | 6 | 7 | 7 | 8 | 8 | 7.2 | 100 |
| oral 8 × 10 mg/kg | (13) 3.3 | 5 | 9 | 10 | 11 | 13 | 13 | 11.2 | 180.6 |
| | (16) 4.2 | 5 | 5 | 6 | 6 | 7 | 7 | 6.2 | 106.8 |
| | (16) 4.4 | 5 | 5 | 6 | 6 | 7 | 8 | 6.4 | 110.3 |
| | ketoconazole | 5 | 5 | 6 | 6 | 6 | 6 | 5.8 | 100 |
| subcutaneous 8 × 30 mg/kg | (13) 3.3 | 5 | 11 | 12 | 12 | 14 | 14 | 12.6 | 153.6 |
| | (16) 4.2 | 5 | 8 | 9 | 11 | 13 | 14 | 11.0 | 134.1 |
| | (16) 4.4 | 5 | 8 | 9 | 10 | 12 | 14 | 10.6 | 129.2 |
| | ketoconazole | 5 | 7 | 7 | 8 | 8 | 11 | 8.2 | 100 |
| subcutaneous 8 × 10 mg/kg | (13) 3.3 | 5 | 10 | 11 | 11 | 11 | 13 | 11.2 | 233.3 |
| | (16) 4.2 | 5 | 7 | 8 | 8 | 11 | 11 | 9.0 | 187.5 |
| | (16) 4.4 | 5 | 5 | 7 | 7 | 7 | 8 | 6.8 | 141.6 |
| | ketoconazole | 5 | 4 | 4 | 5 | 5 | 6 | 4.8 | 100 |
| Controls, untreated infected animals | — | 10 | 1 1 2 | 1 1 2 | 1 1 3 | 2 2 3 | 2 2 3 | 2.0 | 30.3 |

We claim:

1. A compound of the formula I

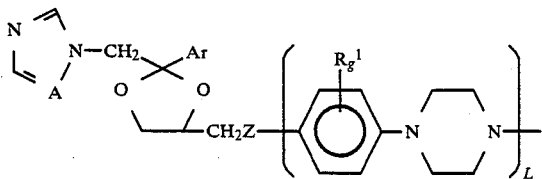

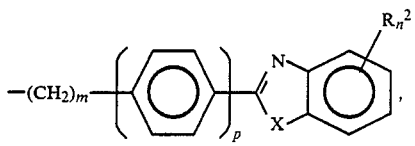

in which:
A is CH or N,
Ar is a phenyl group which is unsubstituted or carries up to 2 substituents which are identical or different and are F, Cl, Br or $C_6H_5$,
Z is O or, if L, m and p simultaneously are zero, is O or S,
$R^1$ is $C_1$-$C_3$-alkyl, F or Cl,
g is 0, 1 or 2,
L is 0 or 1,
m is 0, 1, 2, 3 or 4,
p is 0 or, if m does not equal 0 or if L and m are simultaneously 0, is 0 or 1,
X is O or, if m does not equal 0 or if L, m and p are simultaneously 0, is O or S,
$R^2$, independently of one another, are $C_1$-$C_4$-alkyl, $C_1$-$C_4$-alkoxy, F, Cl, Br, I, $SCH_3$, $CO$-$C_6H_5$, $CF_3$, $COOCH_3$, $COOC_2H_5$ or $NO_2$, and
n is 0, 1 or 2,
and the physiologically acceptable acid-addition salt thereof.

2. A compound of the formula I as claimed in claim 1, in which at least one of the substituents and indices has the following meaning:
A is CH or N,
Ar is a phenyl group which is substituted by 1 or 2 F or Cl atoms,
Z is O or, if L, m and p simultaneously are zero, is O or S, $R^1$ is $CH_3$ or $C_2H_5$,
g is 0 or 2,
L is 0 or 1,
m is 0, 1, 2 or 3,
p is 0 or, if m is 1, is 0 or 1,
x is O or, if m is 1, 2 or 3, or if L and m are simultaneously 0, or if, simultaneously, m is 0 and n is 1 or 2, is O or S,
$R^2$, independently of one another, are $C_1$-$C_4$-n-alkyl, $C_1$-$C_4$-alkoxy, F, Cl or Br, and
n is 0, 1 or 2.

3. A compound of the formula I as claimed in claim 1, in which at least one of the substituents and indices has the following meaning:
A is CH or N,
Ar is 2,4-dichlorophenyl,
Z is O,
$R^1$ is $CH_3$,
g is 0 or 2,
L is 0 or 1,
m is 0, 1, 2 or 3,
p is 0 or, if m is 1, is 0 or 1,
X is O or, if m is 1, 2 or 3 or if L and m are simultaneously 0, is O or S,
$R^2$, independently of one another, are $CH_3$, $C_2H_5$, $C_1$-$C_4$-alkoxy, F, Cl or Br and
n is 0, 1 or 2.

4. A compound of the formula I as claimed in claim 1, wherein L, m and p simultaneously are zero, or L is zero and m and p simultaneously are 1, and in each case X is O or S and n is zero or 1, and $R^2$ is $CH_3$, $C_2H_5$, $C_1$-$C_4$-alkoxy, F, Cl or Br.

5. A compound I as claimed in claim 1, wherein the azolylmethyl radical and the piperazinophenoxymethyl group in the 4 position on the dioxolane are in the cis position.

6. A pharmaceutical composition having antimycotic action comprising an invert carrier material and as an active ingredient an antimycotically effective amount of a compound as claimed in claim 1.

7. A process for the treatment of mycoses, wherein an active amount of a compound I as claimed in claim 1, is administered together with pharmaceutically suitable excipients.

* * * * *